(12) United States Patent
Ivri

(10) Patent No.: US 12,290,472 B2
(45) Date of Patent: *May 6, 2025

(54) HYDRODYNAMICALLY ACTUATED PRESERVATIVE FREE DISPENSING SYSTEM

(71) Applicant: Bausch + Lomb Ireland Limited, Dublin (IE)

(72) Inventor: Yehuda Ivri, Newport Coast, CA (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 355 days.

This patent is subject to a terminal disclaimer.

(21) Appl. No.: 17/692,991

(22) Filed: Mar. 11, 2022

(65) Prior Publication Data

US 2022/0192874 A1 Jun. 23, 2022

Related U.S. Application Data

(63) Continuation-in-part of application No. 17/509,383, filed on Oct. 25, 2021, now Pat. No. 11,938,057, (Continued)

(51) Int. Cl.
*A61F 9/00* (2006.01)

(52) U.S. Cl.
CPC .................. *A61F 9/0026* (2013.01)

(58) Field of Classification Search
CPC .... A61F 9/0008; A61F 9/0026; A61F 9/0017; A61F 9/00; A61F 9/007; A61M 11/005;
(Continued)

(56) References Cited

U.S. PATENT DOCUMENTS

| | | | |
|---|---|---|---|
| 3,640,274 | A | 2/1972 | Costello |
| 3,779,245 | A | 12/1973 | Windsor |

(Continued)

FOREIGN PATENT DOCUMENTS

| | | | |
|---|---|---|---|
| CN | 103118642 | A | 5/2013 |
| CN | 104146816 | A | 11/2014 |

(Continued)

OTHER PUBLICATIONS

Marx et al., "Opthalmic Squeeze Dispenser: Eliminating the Need for Additives in Multidose Preservative-Free Eyecare Formulations", 2017, Drug Development & Delivery, vol. 17, pp. 40-44.

(Continued)

*Primary Examiner* — Guy K Townsend
*Assistant Examiner* — Seth Han
(74) *Attorney, Agent, or Firm* — Perilla Knox & Hildebrandt LLP; Stephanie Davy-Jow

(57) ABSTRACT

Multi-dose preservative-free ocular fluid delivery devices are provided. The fluid delivery device includes a fluid dispensing system and a fluid package for storing a liquid therein and supplying said liquid to the dispensing system. The dispensing system comprises an elongated chamber which includes a check valve which defines a frontal closure to the chamber. The valve is normally closed and hermetically seals the chamber. The dispenser includes a vibration motor that induces oscillations to the chamber and to the fluid within. The oscillations of the chamber impart momentum to the fluid stored in the chamber which in turn imparts force that cyclically opens the valve to dispense streams or liquid droplets. Fluid is dispensed only when the motor oscillates while otherwise the valve is hermetically closed. Preferably, the fluid package and check valve are included in a disposable reservoir assembly.

11 Claims, 16 Drawing Sheets

Related U.S. Application Data which is a continuation-in-part of application No. 17/233,105, filed on Apr. 16, 2021, now Pat. No. 11,925,577.

(60) Provisional application No. 63/212,545, filed on Jun. 18, 2021, provisional application No. 63/159,830, filed on Mar. 11, 2021, provisional application No. 63/011,808, filed on Apr. 17, 2020.

(58) Field of Classification Search
CPC ........... A61M 15/025; F04B 7/02; F04B 9/12; B05B 11/0005; B05B 11/007; B05B 17/0646; B05B 1/02; B05B 11/0064; B05B 11/0067; B05B 17/0638
See application file for complete search history.

(56) References Cited

U.S. PATENT DOCUMENTS

| | | |
|---|---|---|
| 3,812,854 A | 5/1974 | Michaels et al. |
| 3,861,386 A | 1/1975 | Harris et al. |
| 3,934,585 A | 1/1976 | Maurice |
| 3,970,250 A | 7/1976 | Drews |
| 3,976,072 A | 8/1976 | Walker |
| 4,159,803 A | 7/1979 | Cameto et al. |
| 4,300,546 A | 11/1981 | Kruber |
| 4,334,531 A | 6/1982 | Reichl et al. |
| 4,338,576 A | 7/1982 | Takahashi et al. |
| 4,344,744 A | 8/1982 | Schuster et al. |
| 4,352,459 A | 10/1982 | Berger et al. |
| 4,465,234 A | 8/1984 | Maehara et al. |
| 4,632,311 A | 12/1986 | Nakane et al. |
| 4,655,393 A | 4/1987 | Berger |
| 4,793,339 A | 12/1988 | Matsumoto et al. |
| 4,850,534 A | 7/1989 | Takahashi et al. |
| 4,882,150 A | 11/1989 | Kaufman |
| 4,952,581 A | 8/1990 | Bito et al. |
| 4,961,345 A | 10/1990 | Tsuruoka et al. |
| 4,976,259 A | 12/1990 | Higson et al. |
| 4,981,625 A | 1/1991 | Rhim et al. |
| 5,025,957 A | 6/1991 | Ranalletta et al. |
| 5,171,306 A | 12/1992 | Vo |
| 5,232,363 A | 8/1993 | Meller |
| 5,368,582 A | 11/1994 | Bertera |
| 5,370,317 A | 12/1994 | Weston |
| 5,487,378 A | 1/1996 | Robertson et al. |
| 5,549,249 A | 8/1996 | Foster et al. |
| 5,624,057 A | 4/1997 | Lifshey |
| 5,627,611 A | 5/1997 | Scheiner |
| 5,630,793 A | 5/1997 | Rowe |
| 5,657,926 A | 8/1997 | Toda |
| 5,692,651 A | 12/1997 | Fuchs |
| 5,811,443 A | 9/1998 | DeSantis, Jr. et al. |
| 5,828,394 A | 10/1998 | Khuri-Yakub et al. |
| 5,938,117 A | 8/1999 | Ivri |
| 5,958,342 A | 9/1999 | Gamble et al. |
| 5,960,224 A | 9/1999 | Sanada et al. |
| 6,024,717 A | 2/2000 | Ball et al. |
| 6,062,212 A | 5/2000 | Davison et al. |
| 6,065,623 A | 5/2000 | Hierzer et al. |
| 6,095,376 A | 8/2000 | Hennemann et al. |
| 6,196,218 B1 | 3/2001 | Voges |
| 6,232,129 B1 | 5/2001 | Wiktor |
| 6,273,092 B1 | 8/2001 | Nolan |
| 6,302,101 B1* | 10/2001 | Py ................... B05B 11/1066 128/200.22 |
| 6,467,476 B1 | 10/2002 | Ivri et al. |
| RE38,077 E | 4/2003 | Cohen et al. |
| 6,543,442 B2 | 4/2003 | Gonda et al. |
| 6,629,646 B1 | 10/2003 | Ivri |
| 6,730,066 B1 | 5/2004 | Bennwik et al. |
| 6,758,837 B2 | 7/2004 | Péclat et al. |
| 6,869,275 B2 | 3/2005 | Dante et al. |
| 7,066,398 B2 | 6/2006 | Borland et al. |
| 7,105,357 B1 | 9/2006 | Kalkum et al. |
| 7,201,732 B2 | 4/2007 | Anderson et al. |
| 7,314,938 B2 | 1/2008 | Shen et al. |
| 7,571,722 B2 | 8/2009 | Wuttke et al. |
| 7,745,460 B2 | 6/2010 | Shen et al. |
| 7,790,743 B2 | 9/2010 | Shen et al. |
| 7,874,467 B2 | 1/2011 | Pardes et al. |
| 7,883,031 B2 | 2/2011 | Collins, Jr. et al. |
| 7,928,122 B2 | 4/2011 | Shen et al. |
| 8,012,136 B2 | 9/2011 | Collins, Jr. et al. |
| 8,048,047 B2 | 11/2011 | Domash |
| 8,056,766 B2 | 11/2011 | Grevin |
| 8,128,606 B2 | 3/2012 | Anderson et al. |
| 8,133,210 B2 | 3/2012 | Al-Abdulla et al. |
| 8,144,399 B2 | 3/2012 | Steenblik et al. |
| 8,168,655 B2 | 5/2012 | Gadek et al. |
| 8,273,307 B2 | 9/2012 | Eickhoff et al. |
| 8,367,701 B2 | 2/2013 | Burnier et al. |
| 8,398,001 B2 | 3/2013 | Borland et al. |
| 8,435,544 B2 | 5/2013 | Mitra et al. |
| 8,544,462 B2 | 10/2013 | Papania et al. |
| 8,545,463 B2 | 10/2013 | Collins, Jr. et al. |
| 8,592,450 B2 | 11/2013 | Gadek et al. |
| 8,629,111 B2 | 1/2014 | Acheampong et al. |
| 8,633,162 B2 | 1/2014 | Acheampong et al. |
| 8,642,556 B2 | 2/2014 | Acheampong et al. |
| 8,648,048 B2 | 2/2014 | Acheampong et al. |
| 8,684,980 B2 | 4/2014 | Hunter et al. |
| 8,685,930 B2 | 4/2014 | Acheampong et al. |
| 8,722,728 B2 | 5/2014 | Wong et al. |
| 8,733,935 B2 | 5/2014 | Ballou, Jr. et al. |
| 8,863,998 B2 | 10/2014 | Painchaud et al. |
| 8,927,574 B2 | 1/2015 | Burnier |
| 8,927,921 B1 | 1/2015 | Nelms et al. |
| 8,936,021 B2 | 1/2015 | Collins, Jr. |
| 9,039,666 B2 | 5/2015 | Voss et al. |
| 9,068,566 B2 | 6/2015 | Ivri |
| 9,085,553 B2 | 7/2015 | Zeller et al. |
| 9,087,145 B2 | 7/2015 | Ballou, Jr. et al. |
| 9,186,690 B2 | 11/2015 | Scanlon et al. |
| 9,216,174 B2 | 12/2015 | Shen et al. |
| 9,238,532 B2 | 1/2016 | Decock et al. |
| 9,248,191 B2 | 2/2016 | Acheampong et al. |
| 9,353,088 B2 | 5/2016 | Burnier |
| 9,447,077 B2 | 9/2016 | Burnier |
| 9,597,230 B2 | 3/2017 | Haffner et al. |
| 9,676,525 B2 | 6/2017 | Greiner-Perth et al. |
| 9,700,686 B2 | 7/2017 | Gavini et al. |
| 9,801,757 B2 | 10/2017 | Voss et al. |
| 9,808,825 B2 | 11/2017 | Aguilar et al. |
| 9,867,933 B2 | 1/2018 | Pardes et al. |
| 9,890,141 B2 | 2/2018 | Burnier |
| 10,073,949 B2 | 9/2018 | Shen et al. |
| 10,105,720 B2 | 10/2018 | Decock et al. |
| 10,124,000 B2 | 11/2018 | Shen |
| 10,154,923 B2 | 12/2018 | Hunter et al. |
| 10,174,017 B2 | 1/2019 | deLong et al. |
| 10,314,740 B2 | 6/2019 | Kraft |
| 10,624,781 B2 | 4/2020 | Ivri |
| 11,278,448 B2 | 3/2022 | Palanker et al. |
| 2001/0035184 A1 | 11/2001 | Schuler et al. |
| 2001/0036424 A1 | 11/2001 | Takahashi et al. |
| 2001/0036449 A1 | 11/2001 | Garst |
| 2002/0078947 A1 | 6/2002 | Gumaste |
| 2002/0124843 A1 | 9/2002 | Skiba et al. |
| 2002/0158196 A1 | 10/2002 | Berggren et al. |
| 2002/0161344 A1 | 10/2002 | Peclat et al. |
| 2002/0185125 A1 | 12/2002 | Klimowicz et al. |
| 2002/0190079 A1 | 12/2002 | Hamamoto |
| 2003/0052573 A1 | 3/2003 | Wischnewskiy |
| 2003/0065294 A1 | 4/2003 | Pickup et al. |
| 2003/0071071 A1 | 4/2003 | Garcia et al. |
| 2003/0140921 A1 | 7/2003 | Smith et al. |
| 2004/0039355 A1 | 2/2004 | Gonzalez et al. |
| 2004/0050861 A1 | 3/2004 | Lisec et al. |
| 2004/0138630 A1 | 7/2004 | Al-Abdulla et al. |
| 2004/0163645 A1 | 8/2004 | Connelly et al. |
| 2004/0173642 A1 | 9/2004 | Clifford et al. |
| 2004/0204674 A1 | 10/2004 | Anderson et al. |

(56) References Cited

U.S. PATENT DOCUMENTS

| | | |
|---|---|---|
| 2004/0215157 A1 | 10/2004 | Peclat et al. |
| 2004/0256487 A1 | 12/2004 | Collins, Jr. et al. |
| 2004/0263567 A1 | 12/2004 | Hess et al. |
| 2005/0001981 A1 | 1/2005 | Anderson et al. |
| 2005/0006417 A1 | 1/2005 | Nicol et al. |
| 2005/0107832 A1 | 5/2005 | Bernabei |
| 2005/0172962 A1 | 8/2005 | Gumaste et al. |
| 2005/0207917 A1 | 9/2005 | Koerner et al. |
| 2005/0214129 A1 | 9/2005 | Greene et al. |
| 2005/0240162 A1 | 10/2005 | Chen et al. |
| 2005/0261641 A1 | 11/2005 | Warchol et al. |
| 2006/0065677 A1 | 3/2006 | Py et al. |
| 2006/0069358 A1 | 3/2006 | Gerondale |
| 2006/0147313 A1 | 7/2006 | Zengerle et al. |
| 2006/0210604 A1 | 9/2006 | Dadey et al. |
| 2007/0051362 A1 | 3/2007 | Sullivan et al. |
| 2007/0088267 A1 | 4/2007 | Shekalim |
| 2007/0088268 A1 | 4/2007 | Edwards |
| 2007/0102455 A1 | 5/2007 | Stark et al. |
| 2007/0119969 A1 | 5/2007 | Collins, Jr. et al. |
| 2007/0195151 A1 | 8/2007 | Anderson et al. |
| 2007/0268340 A1 | 11/2007 | Dacquay et al. |
| 2007/0295332 A1 | 12/2007 | Ziegler et al. |
| 2008/0039807 A1 | 2/2008 | Pine |
| 2008/0202514 A1 | 8/2008 | Kriksunov et al. |
| 2008/0214940 A1 | 9/2008 | Benaron et al. |
| 2008/0233053 A1 | 9/2008 | Gross et al. |
| 2008/0247264 A1 | 10/2008 | Gabl et al. |
| 2008/0257911 A1 | 10/2008 | Choi et al. |
| 2009/0060793 A1 | 3/2009 | Eickhoff et al. |
| 2009/0114742 A1 | 5/2009 | Collins, Jr. |
| 2009/0134235 A1 | 5/2009 | Ivri |
| 2009/0182291 A1 | 7/2009 | Eilat |
| 2009/0192443 A1 | 7/2009 | Collins, Jr. |
| 2009/0212127 A1 | 8/2009 | Reynolds et al. |
| 2009/0212133 A1 | 8/2009 | Collins, Jr. et al. |
| 2009/0223513 A1 | 9/2009 | Papania et al. |
| 2010/0001090 A1 | 1/2010 | Neergaard et al. |
| 2010/0005903 A1 | 1/2010 | Beavis |
| 2010/0013352 A1 | 1/2010 | Pletner et al. |
| 2010/0044460 A1 | 2/2010 | Sauzade |
| 2010/0072301 A1 | 3/2010 | Cater |
| 2010/0072302 A1 | 3/2010 | Cater |
| 2010/0076388 A1 | 3/2010 | Cater |
| 2010/0147899 A1 | 6/2010 | Nardi |
| 2010/0186738 A1 | 7/2010 | Kobayashi et al. |
| 2010/0222752 A1 | 9/2010 | Collins, Jr. et al. |
| 2010/0236545 A1 | 9/2010 | Kern |
| 2010/0295420 A1 | 11/2010 | Wierach |
| 2010/0326431 A1 | 12/2010 | Yu |
| 2011/0074247 A1 | 3/2011 | Hohlfeld et al. |
| 2011/0102735 A1 | 5/2011 | Gupta et al. |
| 2011/0106025 A1 | 5/2011 | Hall et al. |
| 2011/0146670 A1 | 6/2011 | Gallem et al. |
| 2011/0203580 A1* | 8/2011 | Papania ............ A61M 15/0065 |
| | | 128/200.14 |
| 2011/0284579 A1 | 11/2011 | Pardes et al. |
| 2011/0293452 A1 | 12/2011 | Kim et al. |
| 2011/0305425 A1 | 12/2011 | Fabrykowski et al. |
| 2012/0017898 A1 | 1/2012 | Moller |
| 2012/0062840 A1 | 3/2012 | Ballou, Jr. et al. |
| 2012/0070467 A1 | 3/2012 | Ballou, Jr. et al. |
| 2012/0143152 A1 | 6/2012 | Hunter et al. |
| 2012/0179122 A1 | 7/2012 | Eilat et al. |
| 2012/0197219 A1 | 8/2012 | Scanlon et al. |
| 2012/0304929 A1 | 12/2012 | Ivri |
| 2013/0002095 A1 | 1/2013 | Van der Linden |
| 2013/0017283 A1 | 1/2013 | Zemel et al. |
| 2013/0025038 A1 | 1/2013 | Frey et al. |
| 2013/0053042 A1 | 2/2013 | Tanikawa et al. |
| 2013/0079733 A1 | 3/2013 | Burt et al. |
| 2013/0118619 A1 | 5/2013 | Loth et al. |
| 2013/0140225 A1 | 6/2013 | Decock et al. |
| 2013/0150812 A1 | 6/2013 | Hunter et al. |
| 2013/0152796 A1 | 6/2013 | Pawl |
| 2013/0153677 A1 | 6/2013 | Leen et al. |
| 2013/0164436 A1 | 6/2013 | Yagi et al. |
| 2013/0172830 A1 | 7/2013 | Hunter et al. |
| 2013/0206857 A1 | 8/2013 | Ivri |
| 2013/0299607 A1 | 11/2013 | Wilkerson et al. |
| 2013/0345672 A1 | 12/2013 | Ferreri et al. |
| 2014/0088524 A1 | 3/2014 | Marx |
| 2014/0113946 A1 | 4/2014 | Abad |
| 2014/0157956 A1 | 6/2014 | Date et al. |
| 2014/0171490 A1 | 6/2014 | Gross et al. |
| 2014/0187969 A1* | 7/2014 | Hunter .................. A61B 3/14 |
| | | 604/521 |
| 2014/0214024 A1 | 7/2014 | Eichler |
| 2014/0224267 A1 | 8/2014 | Levitz et al. |
| 2014/0242022 A1 | 8/2014 | Vehige et al. |
| 2014/0249491 A1 | 9/2014 | Ballou, Jr. et al. |
| 2014/0257172 A1 | 9/2014 | Yalamanchili |
| 2014/0274910 A1 | 9/2014 | Cumberlidge et al. |
| 2014/0276054 A1 | 9/2014 | Hossack et al. |
| 2014/0285121 A1 | 9/2014 | Balogh et al. |
| 2014/0323931 A1 | 10/2014 | Avni |
| 2014/0336596 A1 | 11/2014 | Wochele |
| 2014/0336618 A1 | 11/2014 | Wilkerson et al. |
| 2015/0018781 A1* | 1/2015 | Rinderknect ......... A61F 9/0026 |
| | | 604/298 |
| 2015/0035180 A1 | 2/2015 | Rinderknect et al. |
| 2015/0036219 A1 | 2/2015 | Rinderknect et al. |
| 2015/0040891 A1 | 2/2015 | Avni |
| 2015/0086397 A1 | 3/2015 | Ma |
| 2015/0097050 A1 | 4/2015 | Ciervo |
| 2015/0139973 A1 | 5/2015 | Steinfeld et al. |
| 2015/0144128 A1 | 5/2015 | Hijlkema et al. |
| 2015/0209174 A1 | 7/2015 | Abreu |
| 2015/0209178 A1 | 7/2015 | Blakey et al. |
| 2015/0238689 A1 | 8/2015 | Shimizu |
| 2015/0256730 A1 | 9/2015 | Shen et al. |
| 2015/0276994 A1 | 10/2015 | Shen et al. |
| 2015/0308421 A1 | 10/2015 | Vogt |
| 2015/0328151 A1 | 11/2015 | Ballou, Jr. et al. |
| 2015/0352297 A1 | 12/2015 | Stedman et al. |
| 2016/0107180 A1 | 4/2016 | Decock et al. |
| 2016/0120833 A1 | 5/2016 | Wan et al. |
| 2016/0129467 A1 | 5/2016 | Ciardella et al. |
| 2016/0199225 A1 | 7/2016 | Ivri |
| 2016/0199230 A1 | 7/2016 | Doshi et al. |
| 2016/0213866 A1 | 7/2016 | Tan |
| 2016/0263314 A1 | 9/2016 | Pardes et al. |
| 2016/0296367 A1 | 10/2016 | Ivri |
| 2016/0354559 A1 | 12/2016 | Gavini et al. |
| 2017/0028626 A1 | 2/2017 | Delrot et al. |
| 2017/0136484 A1 | 5/2017 | Wilkerson et al. |
| 2017/0138357 A1* | 5/2017 | Kondo .................. F04B 45/047 |
| 2017/0151088 A1 | 6/2017 | Ballou, Jr. et al. |
| 2017/0156927 A1 | 6/2017 | Richter et al. |
| 2017/0182510 A1 | 6/2017 | Wilkerson et al. |
| 2017/0187969 A1 | 6/2017 | Kitamori et al. |
| 2017/0274159 A1 | 9/2017 | Gavini et al. |
| 2017/0344714 A1 | 11/2017 | Ballou, Jr. et al. |
| 2018/0085251 A1 | 3/2018 | Hunter et al. |
| 2018/0108275 A1 | 4/2018 | Newberry et al. |
| 2018/0116871 A1 | 5/2018 | Hunter et al. |
| 2018/0207030 A1 | 7/2018 | Ivri et al. |
| 2018/0229247 A1 | 8/2018 | Laidler |
| 2018/0236466 A1 | 8/2018 | Laidler |
| 2018/0297053 A1 | 10/2018 | Buckland et al. |
| 2019/0053945 A1 | 2/2019 | Hunter et al. |
| 2019/0074086 A1 | 3/2019 | Ballou, Jr. et al. |
| 2019/0099071 A1 | 4/2019 | Ehrmann |
| 2019/0201656 A1 | 7/2019 | Lacey et al. |
| 2019/0217030 A1 | 7/2019 | Burgess et al. |
| 2019/0314195 A1 | 10/2019 | Ivri et al. |
| 2019/0314196 A1 | 10/2019 | Ivri et al. |
| 2019/0314197 A1 | 10/2019 | Ivri et al. |
| 2019/0314198 A1 | 10/2019 | Ivri et al. |
| 2020/0022416 A1* | 1/2020 | Alarcon ................ A24F 40/57 |
| 2020/0197218 A1 | 6/2020 | Newell et al. |
| 2020/0197220 A1 | 6/2020 | Ivri |
| 2020/0246182 A1 | 8/2020 | Ivri |
| 2020/0281768 A1 | 9/2020 | Quintana et al. |

(56) References Cited

U.S. PATENT DOCUMENTS

| | | |
|---|---|---|
| 2020/0315842 A1 | 10/2020 | Palanker et al. |
| 2020/0330267 A1 | 10/2020 | Li et al. |
| 2021/0128350 A1 | 5/2021 | Ivri et al. |
| 2021/0137732 A1 | 5/2021 | Quintana et al. |
| 2021/0220169 A1 | 7/2021 | Ivri |
| 2021/0322209 A1 | 10/2021 | Ivri |
| 2021/0322210 A1 | 10/2021 | Ivri |
| 2022/0039998 A1 | 2/2022 | Ivri |
| 2022/0125631 A1 | 4/2022 | Ianchulev et al. |
| 2022/0160542 A1 | 5/2022 | Palanker et al. |
| 2022/0192874 A1 | 6/2022 | Ivri |

FOREIGN PATENT DOCUMENTS

| | | |
|---|---|---|
| CN | 104582647 A | 4/2015 |
| CN | 204813955 U | 12/2015 |
| CN | 105351426 A | 2/2016 |
| EP | 0622035 A1 | 11/1994 |
| EP | 0622035 B1 | 3/1999 |
| EP | 1493410 A2 | 1/2005 |
| IN | 107530509 A | 1/2018 |
| JP | H08251948 A | 9/1996 |
| JP | 3055480 U | 1/1999 |
| JP | 2007531577 A | 11/2007 |
| JP | 2013535250 A | 9/2013 |
| KR | 10-1258025 B1 | 4/2013 |
| KR | 10-2013-0054352 A | 5/2013 |
| WO | 1994020875 A3 | 1/1995 |
| WO | 1996000050 A1 | 1/1996 |
| WO | 2000005482 A1 | 2/2000 |
| WO | 2001046134 A1 | 6/2001 |
| WO | 2010078428 A1 | 7/2010 |
| WO | 2012009706 A1 | 1/2012 |
| WO | 2013076682 A1 | 5/2013 |
| WO | 2013090459 A1 | 6/2013 |
| WO | 2013090468 A1 | 6/2013 |
| WO | 2013155201 A2 | 10/2013 |
| WO | 2013158967 A3 | 12/2013 |
| WO | 2016115050 A1 | 7/2016 |
| WO | 2016164830 A1 | 10/2016 |
| WO | 2018136618 A2 | 7/2018 |
| WO | 2018227190 A1 | 12/2018 |
| WO | 2019113483 A1 | 6/2019 |
| WO | 12020010116 A1 | 1/2020 |
| WO | 2002072169 A2 | 9/2022 |

OTHER PUBLICATIONS

International Search Report and Written Opinion dated Jul. 16, 2021 in corresponding International Patent Application No. PCT/US2021/027773 (9 pages).

International Search Report and Written Opinion dated Jul. 16, 2021 in corresponding International Patent Application No. PCT/US2021/027779 (8 pages).

Abidi et al., "Lifilegrast: A Novel Drug for Treatment of Dry Eye Disease", Journal of Pharmacology and Pharmacotherapy, 2016, vol. 7, pp. 194-198.

Ali et al., "Glaucoma and Dry Eye", Ophthalmology, 2009, vol. 116, p. 1232.

Birkhoff et al., "New Devices for Dispensing Ophthalmic Treatments May Be the Key to Managing the Life Cycles of Established Products", 2010, Drug Delivery Technology, vol. 10, pp. 16-21.

Brenton, "CRUK/10/30: TRICON8—Sample collection of ovarian cancer tissues and blood for translational research from patients participating in the CR-UK/MRC ICON8 trial", 2015, online abstract.

Choi et al., "Generation of Controllable Monodispersed Sprays Using Impulse Jet and Charging Techniques", Review of Scientific Instruments, 1990, vol. 61, pp. 1689-1693.

Denion et al., "A 5-Minute Interval between Two Dilating Eye Drops Increases Their Effect", Jul. 19, 2017, Optometry and Vision Science, vol. 94, pp. 838-844.

Electronic Tutorials, "Linear Solenoid Actuator", 2016 [online]; [Retrieved on Oct. 17, 2022], Retrieved from the Internet [URL: https://www.electronics-tutorials.ws/io/io_6.html].

Elert, Glenn, "Spherical mirrors", The Physics Hypertextbook, 2021 [online]; [Retrieved on Oct. 17, 2022], Retrieved from the Internet [URL: https://physics.info/mirrors/].

Gannon, Megan, "The Best Length for Eyelashes, According to Science", Feb. 24, 2015 [online]; [Retrieved on Oct. 17, 2022], Retrieved from the Internet [URL: https://www.livescience.com/49934-optimal-length-for-eyelashes-discovered.html].

Ianchulev et al., "Pharmacodynamic profile of mydriatic agents delivered by ocular piezo-ejection microdosing compared with conventional eyedropper", 2016, Ther. Deliv., vol. 7, pp. 751-760.

Jow et al., "Design and Optimization of Printed Spiral Coils for Efficient Transcutaneous Inductive Power Transmission", IEEE Transactions on Biomedical Circuits and Systems, 2007, vol. 1, pp. 193-202.

Kent, Christopher, "Getting Meds onto the Eye, 21st Century Style", Mar. 15, 2013 [online]; [Retrieved on Aug. 27, 2019], Retrieved from the Internet [URL: https://www.reviewofophthalmology.com/article/getting-meds-onto-the-eye-21st-century-style].

Kompella et al., "ISOPT Clinical Hot Topic Panel Discussion on Ocular Drug Delivery", 2019, J. Ocul. Pharmacol. Ther., vol. 35, pp. 457-465.

Lallemand et al., "Cyclosporine A Delivery to the Eye: A Comprehensive Review of Academic and Industrial Efforts", European Journal of Pharmaceutics and Biopharmaceutics, 2017, vol. 117, pp. 14-28.

Lindblad et al., "Production of Uniform-Sized Liquid Droplets", Journal of Scientific Instruments, 1965, vol. 42, pp. 635-638.

Lux et al., "A Comparative Bioavailability Study of Three Conventional Eye Drops Versus a Single Lyophilisate", Br. J. Ophthalmol., 2003, vol. 87, pp. 436-440.

Macmillan Online Dictionary, "Stream," n.d. [online]; [Retrieved on Dec. 13, 2018]; Retrieved from the Internet [URL: https://macmillandictionary.com/dictionary/american/stream_1#stream_9].

Merriam-Webster, "Clamp," 2019 [online]; [Retrieved on Oct. 25, 2022], Retrieved from the Internet [URL: https://www.merriam-webster.com/dictionary/clamp].

Merriam-Webster, "Collimate," 2020 [online]; [Retrieved on Oct. 17, 2022], Retrieved from the Internet [URL: https://www.merriam-webster.com/dictionary/collimated].

Merriam-Webster, "Stream," n.d. [online]; [Retrieved on Dec. 13, 2018], Retrieved from the Internet [URL: https://www.merriam-webster.com/dictionary/stream].

Murube et al., "Classification of Artificial Tears, I: Composition and Properties", Advanced Experimental Medical Biology, 1998, vol. 438, pp. 693-704.

Murube et al., "Classification of Artificial Tears, II: Additives and Commercial Formulas", Advanced Experimental Medical Biology, 1998, vol. 438, pp. 705-715.

Oxford Online Dictionary, "Stream," n.d. [online]; [Retrieved on Dec. 13, 2018]; Retrieved from the Internet [URL: https://en.oxforddictionaries.com/definition/us/stream].

Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.

Vocabulary.com, "Stream," n.d. [online]; [Retrieved on Dec. 13, 2018]; Retrieved from the Internet [URL: https://www.dictionary.com/stream].

\* cited by examiner

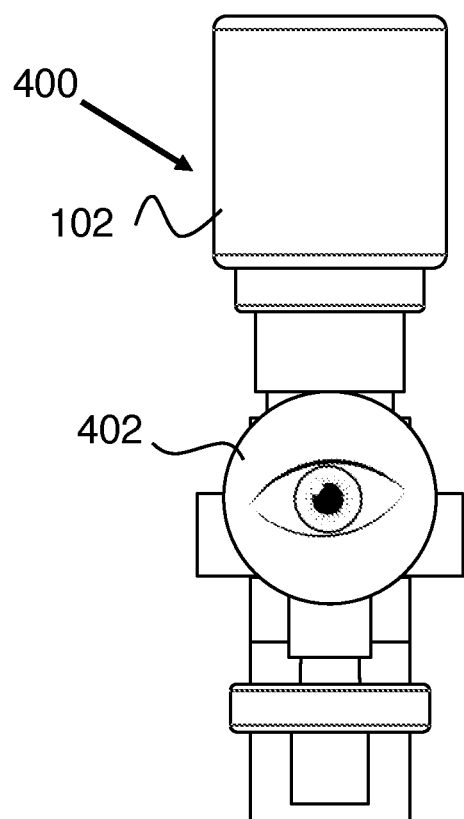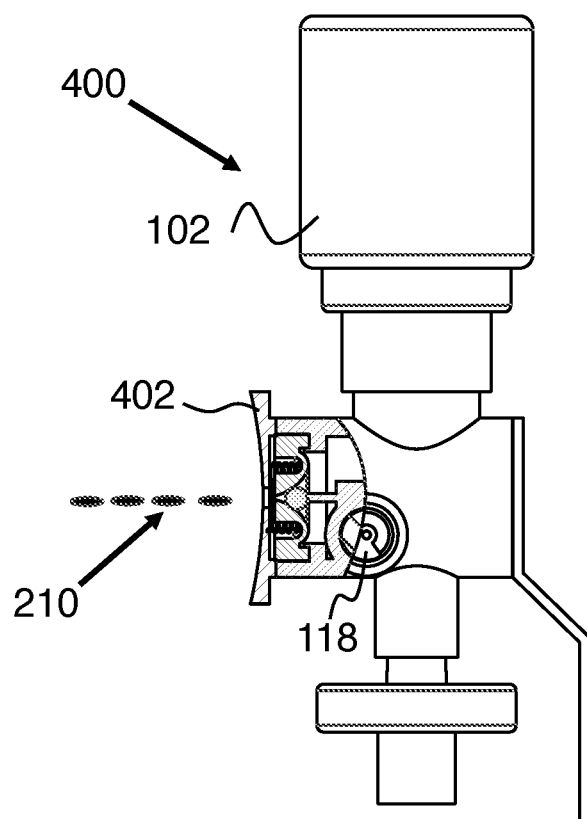
FIG. 4A  FIG. 4B
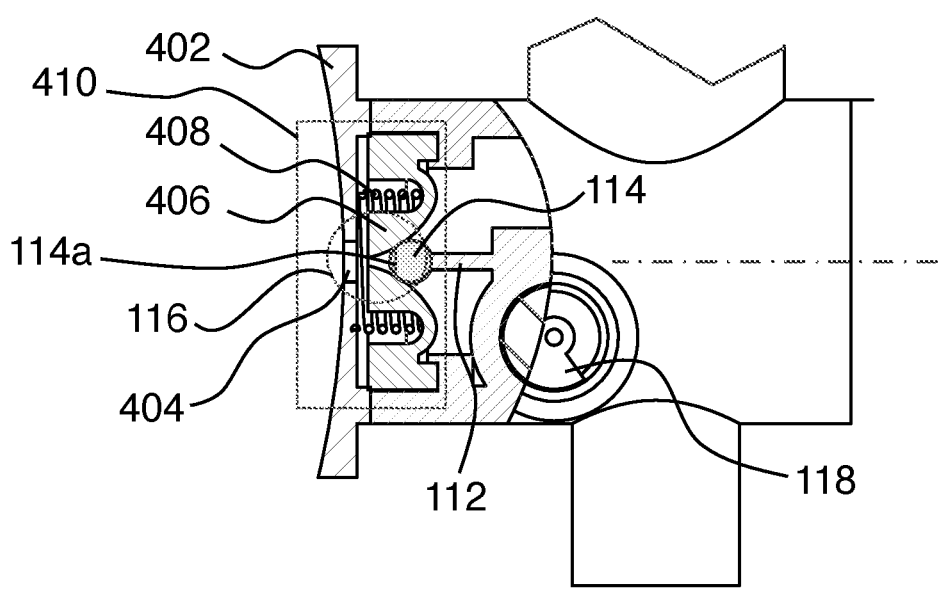
FIG. 4C

HYDRODYNAMICALLY ACTUATED PRESERVATIVE FREE DISPENSING SYSTEM

CROSS REFERENCE TO RELATED APPLICATIONS

This application claims the benefit of U.S. provisional patent application 63/159,830, filed on Mar. 11, 2021, and hereby incorporated by reference in its entirety.

This application claims the benefit of U.S. provisional patent application 63/212,545, filed on Jun. 18, 2021, and hereby incorporated by reference in its entirety.

This application is a continuation in part of U.S. patent application Ser. No. 17/509,383, filed Oct. 25, 2021, and hereby incorporated by reference in its entirety.

Application Ser. No. 17/509,383 is a continuation in part of U.S. patent application Ser. No. 17/233,105, filed Apr. 16, 2021, and hereby incorporated by reference in its entirety.

Application Ser. No. 17/233,105 claims the benefit of U.S. provisional patent application 63/011,808, filed on Apr. 17, 2020, and hereby incorporated by reference in its entirety.

FIELD OF THE INVENTION

The present invention generally pertains to devices for dispensing fluid medicines and more particularly pertains to such devices that store and deliver ophthalmic preservative-free medicines, specifically configured to increase the ease of use and enhance patient compliance with dosing instructions for the medicine.

BACKGROUND

Ease of dispensing fluid medicines and compliance with dosing instructions are primary concerns with all patients. In particular, preservative-free dispensing bottles such as ophthalmic squeeze dispensers typically require greater actuation force due to a valve mechanism that seals the dispensing nozzle to prevent bacterial ingress and contamination. Such system requires much higher pressure to operate and hence much higher squeeze force is required. In addition, prior art dispensing bottles dispense only in an upside-down orientation which require an inconvenient head maneuver and which together with higher actuation force further increases the inconvenience.

Dispensers of the kind in question are known from the prior art, for example from U.S. Pat. Nos. 6,095,376, 9,676,525, US 2014/0336596, US 2016/0107180, U.S. Pat. Nos. 9,238,532, 8,056,766, 8,863,998, and 10,105,720. The dispenser shown in US 2014/0336596 comprises an outlet channel which connects the liquid reservoir to the outlet opening through an outlet valve which is arranged in the outlet channel and which opens when the bottle is squeezed and pressure is generated. Such preservative-free squeeze bottles typically require about 25-28N of squeeze force (Ophthalmic Squeeze Dispenser—*Drug Development and Delivery* October 2017 Vol. 17 No. 7 page 40). Elderly patients, or other patients lacking enough strength and/or dexterity in their hands, often experience problems dispensing medicine from such bottles.

This work provides preservative free ocular dispensing device that can be held horizontally, or in any convenient orientation while the actuation is done effortlessly by an electrical switch. This provides a cost effective solution that is consistent with standard drug packaging processes.

SUMMARY

Multi-dose preservative-free ocular fluid delivery devices are provided. The fluid delivery device includes a fluid dispensing system and a fluid package for storing a liquid therein and supplying said liquid to the dispensing system. The dispensing system comprises an elongated chamber which includes a check valve which defines a frontal closure to the chamber. The valve is normally closed and hermetically seals the chamber. In this work the chamber includes a vibration motor that induces oscillations to the chamber and to the fluid within. The oscillations of the chamber impart momentum to the fluid stored in the chamber which in turn imparts force that cyclically opens the valve to dispense streams or liquid droplets. Fluid is dispensed only when the motor oscillates while otherwise the valve is hermetically closed.

The check valve can include a flexible plate which includes a conical aperture that extends through its thickness, the valve can further include a stationary spherical member that engages tangentially with the inner wall of the conical aperture to create a hermetic sealed closure. The plate can be made of elastomer that has a modulus of elasticity ranging between 0.1-1.2 GPa. The circumference of the plate can be attached to the chamber by a retaining ring that engages with the chamber in an interference fit to create the hermetically sealed closure.

The conical aperture extends through the thickness of the plate such that droplets are dispensed through the smaller opening of the aperture while the larger side of the aperture is in fluid communication with the chamber.

The spherical member may include an antibacterial coating which covers the area of the spherical member that is between the tangential engagement line and the small opening of the aperture.

The vibrational motor oscillates the chamber and the fluid within the chamber. Consequently, cycles of hydrodynamic pulses are generated causing the valve to cyclically open and dispense fluid. Here this phenomenon is characterized by oscillatory interactions between the valve and the surrounding fluid. The hydrodynamic force generated by the momentum of the fluid opens the valve and allows fluid flow through the aperture.

Fluid is dispensed only when the hydrodynamic force is sufficiently high to deform the aperture while otherwise the aperture hermetically seals the chamber. The system prevents ingress of microorganism into the chamber allowing storage of preservative free pharmaceutical. This work provides an electrically operated preservative-free dispensing system that is convenient and cost effective.

BRIEF DESCRIPTION OF THE DRAWINGS

FIG. 4A is a frontal view of an embodiment of the invention.

FIG. 4B is a side view of the embodiment of FIG. 4A.

FIG. 4C is a detail cross sectional view of the embodiment of FIG. 4A.

DETAILED DESCRIPTION

This work describes dispensing devices and methods for delivery of preservative-free solutions or suspensions for ocular administration of ophthalmic drugs. The dispensing devices include a droplet ejecting system that is fluidly connected to an ampoule package containing a liquid to be dispensed. The droplet ejecting system includes a chamber having a check valve that defines a front closure to the chamber. The dispensing system further includes a vibration motor that oscillates the chamber and induces hydrodynamic pulses which consequently causes the valve to cyclically open and eject fluid droplets. The valve is normally closed and hermetically sealing the chamber. The valve opens exclusively in response to hydrodynamic pulses induced by the oscillation of the chamber. In this way fluid is dispensed only when the device is actuated while otherwise the aperture hermetically seals the device and prevents ingress of bacterial and microorganisms thereby allowing storage of preservative-free pharmaceutical formulation. The use of a vibration motor further enables convenient and cost effective, electronically controlled administration.

Figure 1A:
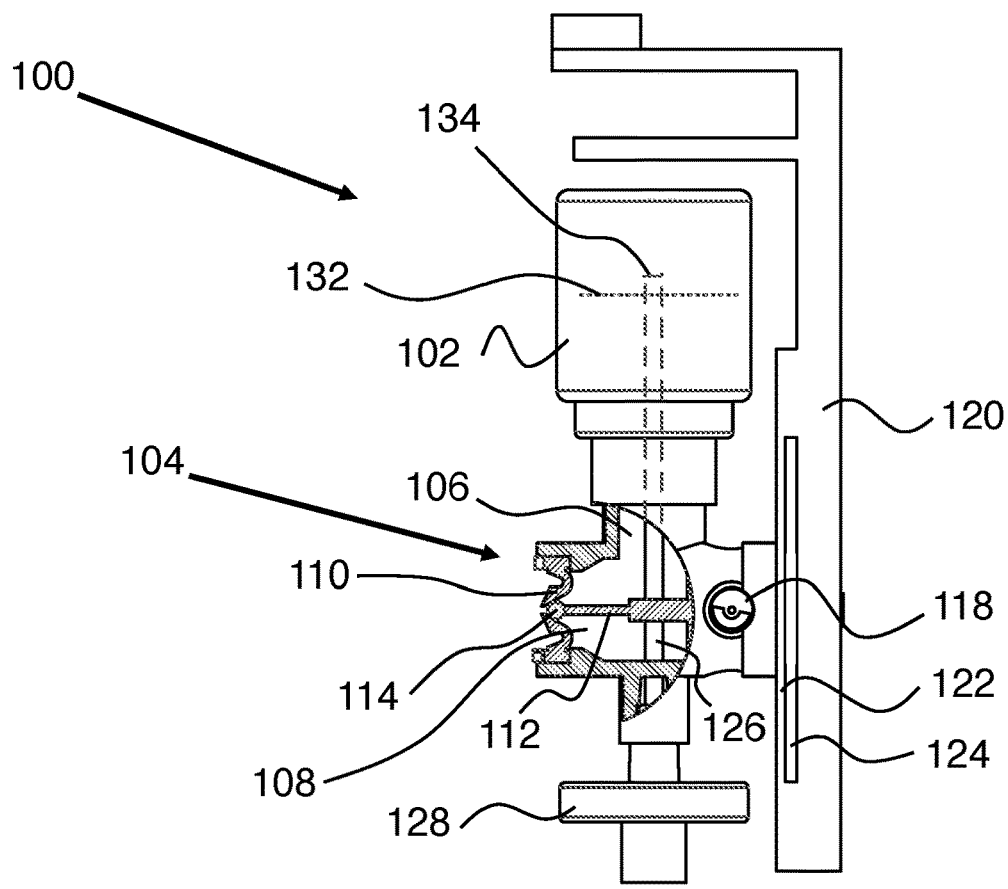
FIG. 1A is a cross sectional view of an embodiment of the invention.
Figure 1B:
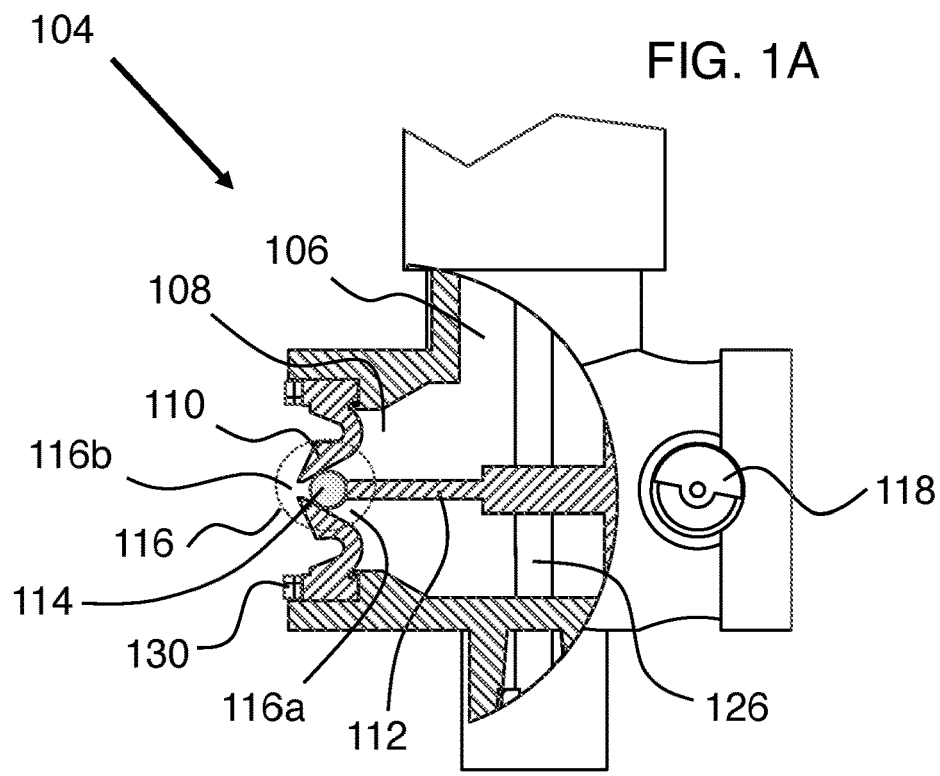
FIG. 1B is a detail cross sectional view of the embodiment of FIG. 1A.

FIG. 1A and FIG. 1B illustrate a side view and an enlarged partial section view, respectively, of a fluid delivery device 100. Delivery device 100 includes a fluid reservoir 102 and dispensing system 104 connected to each other in fluid transmission relationship though passage 106. Dispensing system 104 includes a fluid chamber 108 and also includes a check valve including aperture plate 110 which provides frontal closure to the chamber 108. Referring to FIG. 1B it can be seen that aperture plate 110 includes a conical or tapered aperture 116 (shown inside a dotted circle for clarity) that extends through its center thickness and has a large inlet opening 116*a* in fluid communication with chamber 108 and a smaller exit opening 116*b* though which fluid droplets will be dispensed. Aperture plate 110 can be made of a flexible elastomer such as silicone rubber, VersaFlex, manufactured by VersaFlex Incorporated Kansas City, Kansas USA. Other elastomers with Young modulus of elasticity value between 0.5 GPa to 2 GPa can also be used. Dispensing system 104 further includes a stationary spherical member 114 that tangentially engages in pressure transmission relationship with the inlet opening 116*a* of the conical aperture providing hermetically sealed closure. In a preferred embodiment spherical member 114 is made of high density polyethylene (HDPE) that is harder than silicone thereby creating a tight closure as it engages with the softer aperture plate 110. Spherical member 114 preferably engages in pressure transmission relationship with the conical aperture 116*a* with a preload force of between 0.01N and 0.05N. The combination of aperture plate 110 and spherical member 114 provides a check valve as described above. Spherical member 114 is supported by pin member 112. Member 114 can have a shape other than spherical, since any shape capable of forming a good seal with aperture plate 110 can be used.

Aperture plate 110 can be retained to dispensing system 104 by a retaining ring 130, thereby creating a hermetically sealed closure.

Dispensing system 100 includes a venting tube 126 that is configured to equalize the pressure inside container 102 as the fluid is dispensed from the device. The opening 134 of venting tube 126 is extended above the fluid level 132 at any orientation that the device is held. Vent tube 126 can be connected via a 0.22 micron filter 128 to assure that the air that enters the device is sterile.

Figure 3:
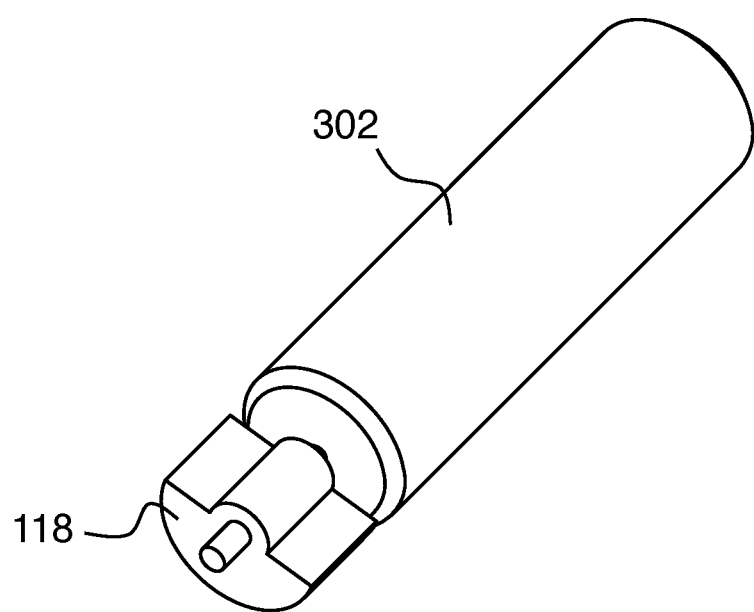
FIG. 3 illustrates a perspective view of a vibration motor as used in embodiments of the invention.

Dispensing system 100 further includes a vibration motor configured to oscillate chamber 108 and the fluid within the chamber. Here this motor is schematically shown as eccentric mechanical load 118 which vibrates the assembly as described when it is rotated by the motor (motor not shown in FIGS. 1A-B, but described below in connection with FIG. 3).

Figure 1C:
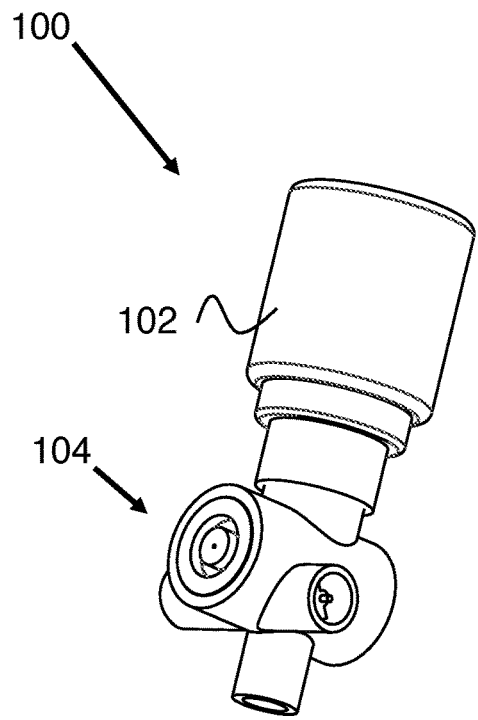
FIG. 1C is a 3D view of the embodiment of FIGS. 1A-B.

FIG. 1C is a 3D view of the embodiment of FIGS. 1A-B.

Figure 2A:
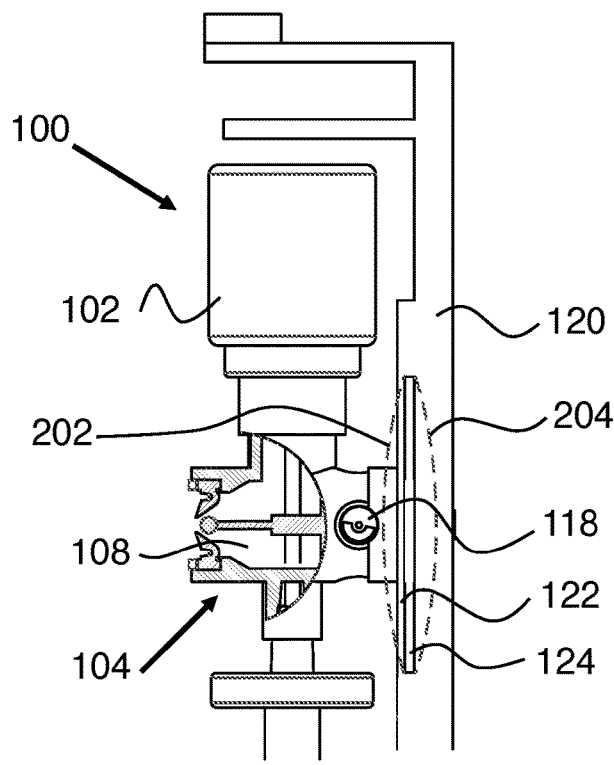
FIG. 2A is a side view and partial cross section view of an embodiment of the invention in operation.
Figure 2B:
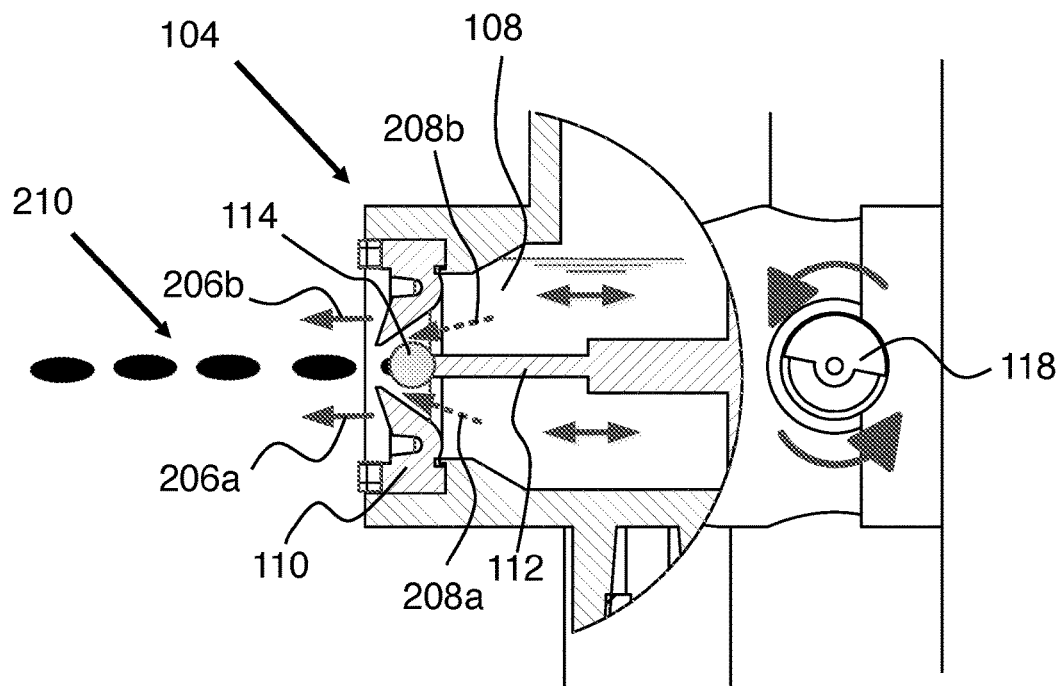
FIG. 2B is a detail cross section view of the example of FIG. 2A.

FIGS. 2A-B illustrate the response of the dispensing system 104 to oscillations. Vibrations of the motor induce oscillation to the body of dispensing system 104 which in turn generates fluid momentum within the chamber due to the dynamical interaction of the fluid with the solid structure of chamber 108. This phenomenon is often referred to as Solid-Fluid-Interaction (SFI). The momentum of the moving fluid exerts force that flexes the aperture plate 110 outwardly in the direction indicated by arrows 206*a* and 206*b* causing the aperture plate 110 to disengage from spherical member 114 thereby opening a fluid flow passage as indicated by the arrows 208*a* and 208*b* and ejection of fluid droplets 210.

Dispensing device 100 is supported by a flexible beam 122 or other structural embodiments which allows it to oscillate freely, as schematically shown by motion excursions 202 and 204. Preferably the spring constant of the beam 122 is 0.05 N/mm to 0.5 N/mm. For example, beam 122 can be formed by fabricating a slot 124 in support structure 120 such that the resulting beam 122 has a thickness suitable for providing a spring constant as recited above.

FIG. 3 illustrates an exemplary vibrational motor 302. The DC Motor 302 of this example has a cylindrical body with a diameter of 4 mm and total length of 17 mm. An eccentric flywheel 118 is attached to the motor shaft. The flywheel has a mass of 1.7 grams with a center of mass about 0.7 mm from the center of rotation. The motor receives 4.5-12 VDC and rotates at 6000-12000 RPM generating centrifugal force of 0.3N at a rotation speed of 8000 RPM. Other DC motors that generate centrifugal force of 0.1-1N and rotation speed of 1000-50000 RPM can be used. The motor can be controlled by a timer circuit which is set to provide an ON time as required to deliver a dose of 8-12 micro-liter. The actuation ON time is 60-200 ms depending on the rheology of the fluid in use. A timer circuit which incorporates a 555 timer IC or a microprocessor-based timer with a 12 volt battery such as A23 alkaline battery may be used.

FIGS. 4A-C illustrate an alternative preferred embodiment of dispensing system 400. FIG. 4A illustrates a frontal view and FIG. 4B illustrates a side view of dispensing system 400. Dispensing system 400 includes a concave mirror 402 which assists in aligning device 400 and fluid stream 210 to the eye of the user. In use, dispensing device 400 is positioned in front of the eye such that the image of the eye appears sharply and in the center of mirror to the user. At this point the device is properly positioned in term of the distance of the eye from mirror-hole 404 and its angular orientation relative to the eye. Upon actuation, stream 210 will be deposited precisely on the corneal surface of the eye. Device 400 preferably includes a 0.22 micron air filter configured to filter the vented air that flows into device 400, as in the previous example.

Device 400 includes a check valve having an aperture plate 406 with a conical aperture 116 that extends through its thickness. The check valve further includes a spherical member 114 that tangentially engages with the inlet opening of the conical aperture 116. In this example, the check valve also includes a compression spring 408 configured to force aperture plate 406 against spherical member 114. In this way a tight seal is created along the engagement line 114a, thus creating a tight and hermetic closure.

Spherical member 114 can be partially covered with an antimicrobial coating, specifically in the area of spherical member 114 that is not in contact with fluid in the chamber. The coated area thus extends between the engagement line 114a and the outlet of the conical aperture (i.e., to the left of 114a on FIG. 4C)). Examples of antimicrobial coatings include silver in metallic form, silver alloy or a non-metallic material that contains silver including salts of silver chloride and silver sulfadiazine. Other optional material includes biguanide derivatives, chlorohexidine diacetate and chlorohexidine digluconate.

Figure 5A:
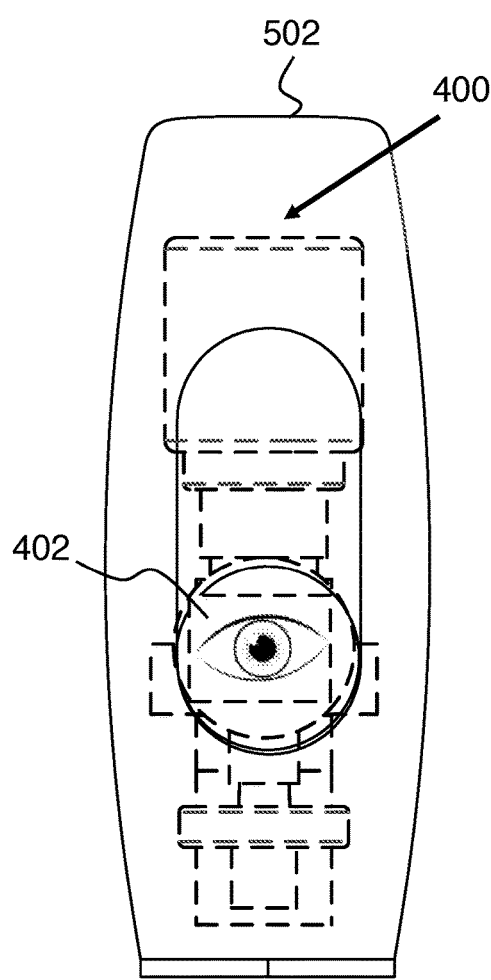
FIG. 5A is a frontal view of an exemplary device enclosed in a housing.
Figure 5B:
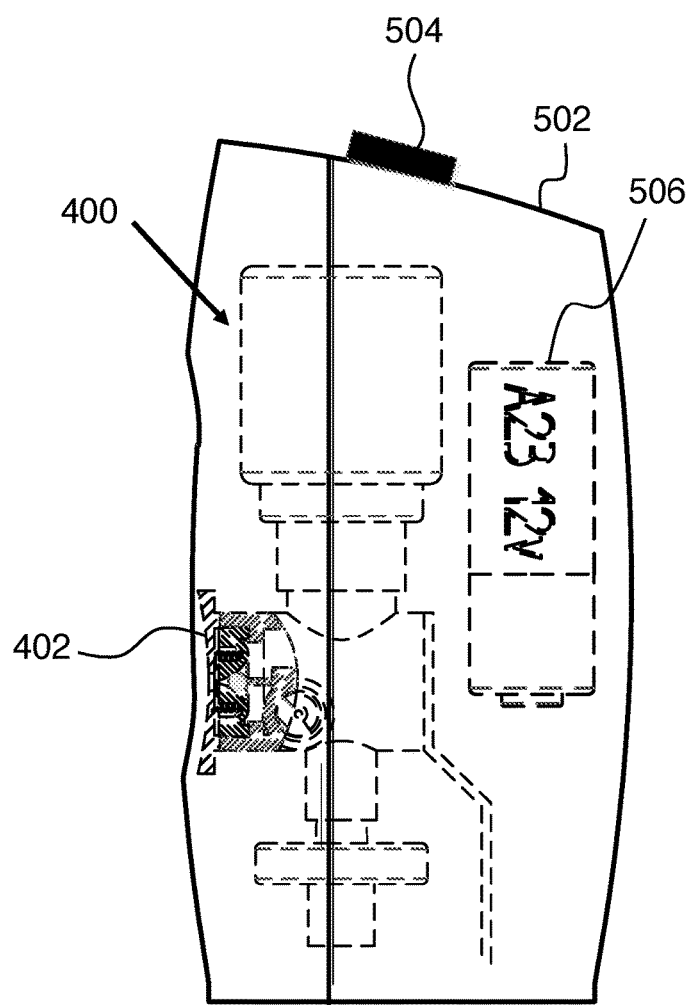
FIG. 5B is a side view of the example of FIG. 5A.

FIGS. 5A-B illustrate frontal and side views, respectively, of a dispensing device 400 packaged in a housing 502. Housing 502 provides a convenient enclosure to the dispensing system 400 that was described in relation in FIGS. 4A-C and is shown with dashed lines here. Housing 502 includes an electrical circuit (not shown) and a 12 volt battery (e.g., type A23) 506. The circuit controls the dispensing period such that a dose of 8-12 microliter is delivered to the ocular surface of the eye. Momentary switch 504 can be used to activate the device 400 such that a stream of droplets is ejected from the aperture as described earlier. FIGS. 5A-B also illustrate the mirror 402 which is visible on the front side of the device. Such a housing can also be used for a dispensing device 100 as described above.

Figures 6A, 6B:
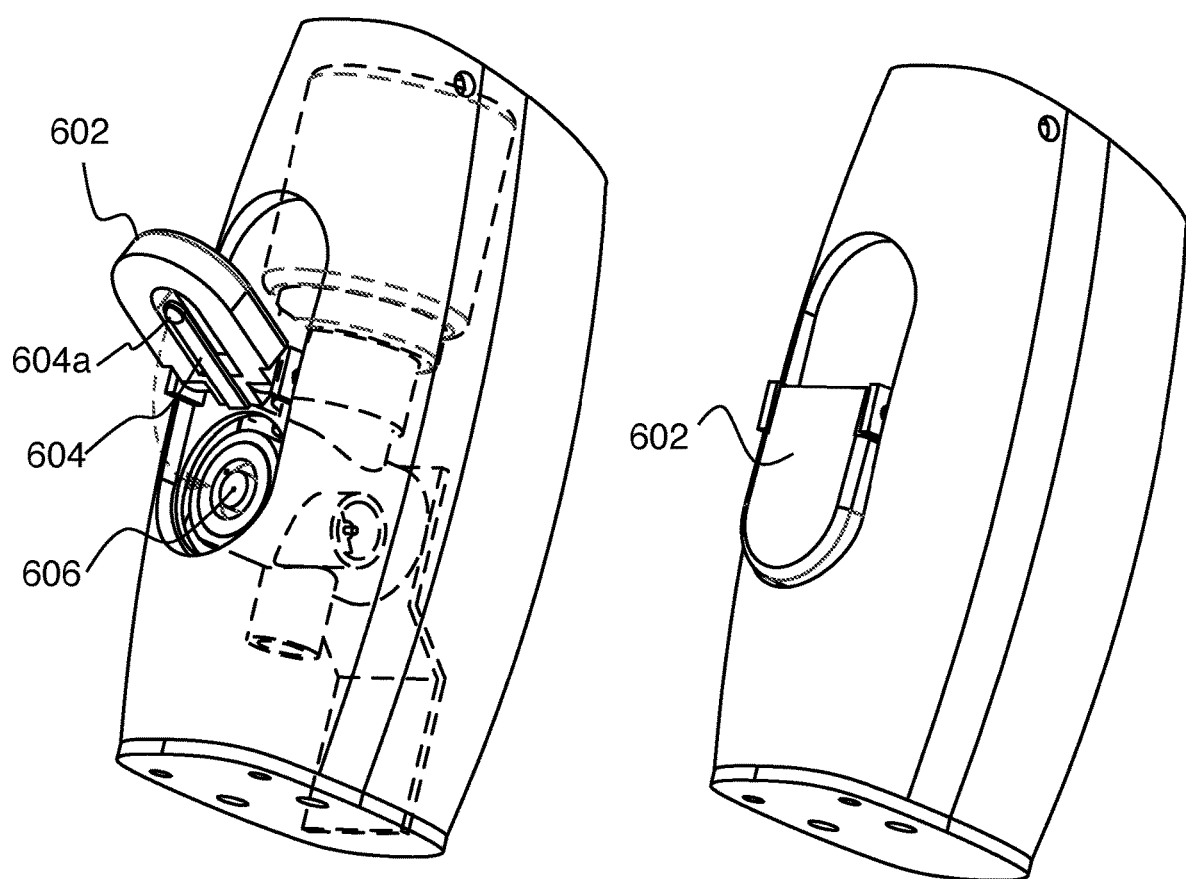
FIGS. 6A-B are perspective views of a device having a housing that includes a swivel cover.

FIGS. 6A-B illustrate some preferred features of housings that can be used with embodiments such as device 100 and device 400 as described above. In this example, the housing includes a swivel cover 602 that covers dispensing nozzle 606 during periods of non-use. Swivel cover 602 provides a means to prevent bacterial contamination on the external areas where a residual fluid may be left following each use. Such residual fluid may contaminate subsequent stream as it is dispensed through the nozzle. Swivel cover 602 preferably includes a flexible member 604 that includes a surface 604a that is covered with antimicrobial coating. Surface 604a engages with the outlet opening of nozzle 606 when the swivel cover 602 is closed as illustrated in FIG. 6B. In this way antipathogen action is achieved. Alternatively, organic dyes with antiseptic action may also be used. For example, toluidine blue, methylene blue, gentian violet and acridine and related active substances such as acridine orange and acridine yellow as well as ethacridine lactate. Germicidal polymers such as polyhexanide are also possible. Materials that contain additives which contain metal-organic substances with an ionizing effect can also be used. Such additives are available from SteriOne GmbH Berlin, Germany. Examples of antimicrobial coatings that can be used on surface 604a include silver in metallic form, silver alloy or a non-metallic material that contains silver including salt of silver chloride and silver sulfadiazine. Other optional material includes biguanide derivatives, chlorohexidine diacetate and chlorohexidine digluconate.

Closed Loop Motor Control

Optionally, the device includes a drive circuit that controls the rotational speed of the motor. The rotational speed of the motor may be inconsistent due to manufacturing tolerance and other factors. Motor speed inconsistency may cause some devices to emit higher dose and some lower dose depending on the speed of the motor.

To prevent such inconsistency the drive circuit that controls the motor can include an optical sensor that measures the rotational speed of the motor and inputs the value to a microprocessor where the measured speed is compared with the desired target speed. The circuit then increases or decreases the power delivered to the motor until it reaches the target speed. The speed of the motor converges to the desired target speed typically within less than 5 actuations and preferably less than two actuations.

The power delivered to the motor can be controlled by Pulse Width Modulation (PWM). PWM is a method of reducing the average power delivered to an electrical motor or other electrical load by effectively applying short and discrete DC pulses at high frequency, typically in the range of 5-15 KHz.

The voltage or current source can be supplied to the motor by means of a repeating series of "on" and "off" pulses. The on-time is the time during which the DC supply is applied to the motor, and the off-time is the period during which that supply is switched off. The density of the on time relative to the density of the off time controls the power delivered to the motor. The microprocessor increases or decrease the on time until the desired speed is reached.

Figure 7A:
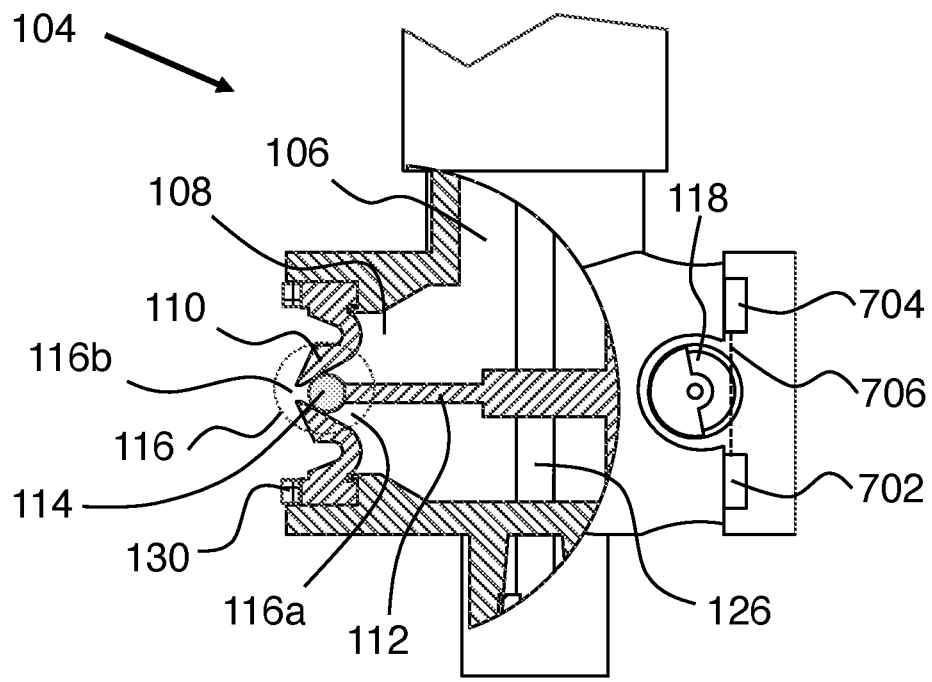
FIGS. 7A-B show operation of an embodiment of the invention including an optical sensor for motor speed.
Figure 7B:
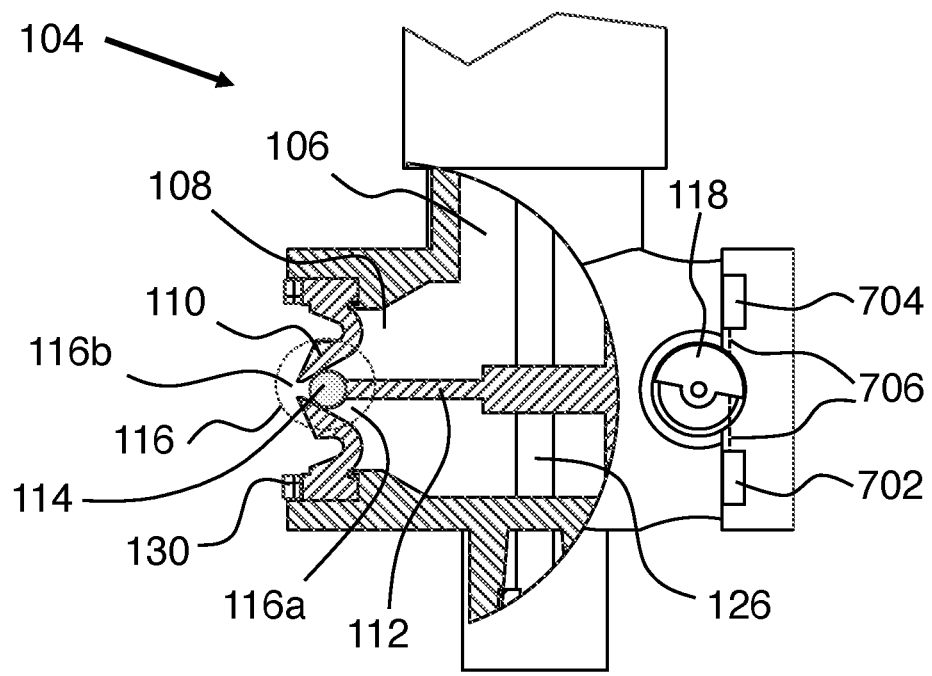

FIGS. 7A-B illustrate the optical sensors that measure the motor speed. The sensors include an LED 702 and a phototransistor 704 positioned coaxially and in predetermined distance from the rotational axis of the motor and its eccentric flywheel 118 such that the flywheel periodically blocks the light. In the first part of the revolution shown in FIG. 7A flywheel 118 is in a rotational position which allow passage of light beam 706 from the LED 702 to reach phototransistor 704 therefore causing the phototransistor to produce an electrical signal. At the second part of the revolution shown in FIG. 7B the light beam 706 from the LED is blocked and interrupted by the flywheel 118. The time between two subsequent interruption signals indicates the cycle time of the motor, the inverse of the cycle time is the number of revolutions per unit time (i.e., the frequency of the motor rotation (which is the same as the frequency of the above-described mechanical excitation)). In this way it is possible to measure the speed of the motor, compare it to the to the target value and make a correction as described earlier.

In this example, an LED is used as the light source and a phototransistor is used as the light detector, but practice of the invention does not depend critically on the choices of optical source and optical detector. Any sources and detectors can be employed.

Disposable Bottle/Reservoir

The present invention also provides a device for actuated delivery of a fluid medicament to the surface of the eye using an easily replaceable reservoir and a reusable coupled base actuation unit. The device can be held horizontally, or in any convenient orientation while the actuation is initiated easily with minimal effort employing an electrical switch attached to the base unit. This approach provides a cost effective solution that is consistent with standard drug packaging processes.

The dispensing system comprises an easily replaceable bottle assembly which includes a disposable ampule, dispensing nozzle, an optional check valve defining a frontal closure to the ampule, which together make up the container closure system. This bottle system is easily removed from a base unit that contacts a surface of the bottle and mechanically actuates it to cause fluid to eject from the nozzle. In one embodiment, the check valve is normally closed and hermetically seals the bottle even when there is not a cap on the bottle. In another embodiment, there is no check valve that closes the aperture of the nozzle. The bottle includes a vibration motor that induces oscillations to the bottle and to the fluid within. The oscillations of the bottle impart momentum to the fluid stored therein which in turn impart force that cyclically opens the valve by creating a pressure gradient to dispense streams or liquid droplets. Fluid droplets are dispensed only when the motor oscillates while otherwise the valve is hermetically closed.

The check valve can include a circular plate made of a flexible elastomer which includes a tapered aperture bounded with outward moving leaflets that extends through its thickness. The valve can further include a stationary spherical member that engages tangentially with the inner wall of conical aperture to result in a hermetically sealed closure when there is no positive pressure gradient between the fluid in the ampule and atmospheric pressure externally. The plate is preferably made of elastomer that has module of elasticity ranging between 0.1-1.2 GPa, which is sufficiently soft to maintain a tight seal between itself and the spherical member in the not extended state. The circumference of the aperture plate can be attached to the chamber by a retaining ring that engages with the chamber in an interference fit to further contribute to a hermetically sealed closure.

The tapered aperture can extend through the thickness of the aperture plate such that droplets are dispensed through the smaller opening of the aperture while the larger side of the aperture is in fluid communication with the bottle.

The spherical member may include an antibacterial coating which covers the area of the spherical member that lays between the tangential engagement line and the small opening of the aperture.

In one embodiment the bottle includes an aperture plate without the check valve. Such embodiment will dispense fluid but will not provide hermetic closure. Embodiments without a valve may be used to dispense fluid that already contain preservatives.

The vibrational motor oscillates the bottle and the fluid within the bottle. The vibration produces cycles of hydrodynamic pulses which by virtue of the positive pressure gradient and hydrodynamic force of the fluid cause the check valve to cyclically open and dispense fluid.

This phenomenon is characterized by oscillatory interactions between the aperture plate and the surrounding fluid. In that, hydrodynamic force generated by the momentum of the fluid open the valve and allows fluid flow through the aperture.

Fluid is dispensed only when the hydrodynamic force is sufficiently high to open the check valve while otherwise the valve hermetically seals the chamber. The system prevents ingress of microorganism into the chamber allowing storage of preservative free pharmaceutical.

The dispensing system is particularly suitable for dispensing viscous eyedrop formulations, particularly lubricating eye drop formulations for treating dry eye syndrome. Such formulations may contain Hydroxypropyl Methyl Cellulose or Propylene glycol having viscosity greater than 50 centipoise or sometime even greater than 110 centipoise.

The ability to dispense viscous solutions is attributed to the large vibratable surface area of the bottle that is in contact with the liquid. Moreover, since the rotation of the motor produced displacement in two directions that are perpendicular to the axis of rotation the fluid-surface interaction is further increased. In an example, this area is larger than 1500 $mm^2$. Additionally, the vibrations are generated by a vibratory rotating mass which applies force in two directions that are perpendicular to the axis of rotation.

The dispensing system advantageously utilizes a disposable bottle while desirably retaining the vibratory assembly for subsequent further uses, thereby providing an economical cost effective and environmentally friendly solution.

An important cost advantage of the present invention relates to the compatibility of the packaging material with the pharmaceutical formulation, manufacturing, and filling processes. Production and filling of ophthalmic medications are highly automated and the processes are regulated, thus using established manufacture processes in new delivery system provides a significant cost advantage. The present invention is a dispensing system that is convenient and cost effective and in addition is better able to handle high viscosity fluid administration. This capability is enabled by optimizing fluid-Solid interactions (SFI), through the design of the interface of the interchangeable coupling mechanism between the removable bottle and motor housing assembly.

The present invention also provides a dispensing device and method for delivery of preservative-free solutions or suspensions specifically but not exclusively for ocular administration of ophthalmic drugs. The dispensing devices comprising a bottle containing a liquid to be dispensed having a dispensing nozzle at one end and a vibratory motor at the second end.

Exemplary dispensing systems of the present invention include a disposable bottle containing ophthalmic solution to be dispensed. The dispensing system also includes a check valve that defines a front closure to the bottle. The bottle further includes a vibrational motor that oscillates the bottle and induces hydrodynamic pulses which consequently cause the check valve to cyclically open and eject fluid droplets. In the present invention the check valve is normally closed and hermetically sealing the bottle. The check valve opens exclusively in response to hydrodynamic pulses induced by the oscillation of the bottle and the fluid therein. In this way fluid is dispensed only when the device is actuated while otherwise the valve hermetically seals the bottle and prevent ingress of bacteria and microorganism thereby allowing storage of preservative-free pharmaceutical formulation. The use of a vibration motor to induce vibration further enables convenient and cost effective, electronically controlled administration.

Figure 8A:
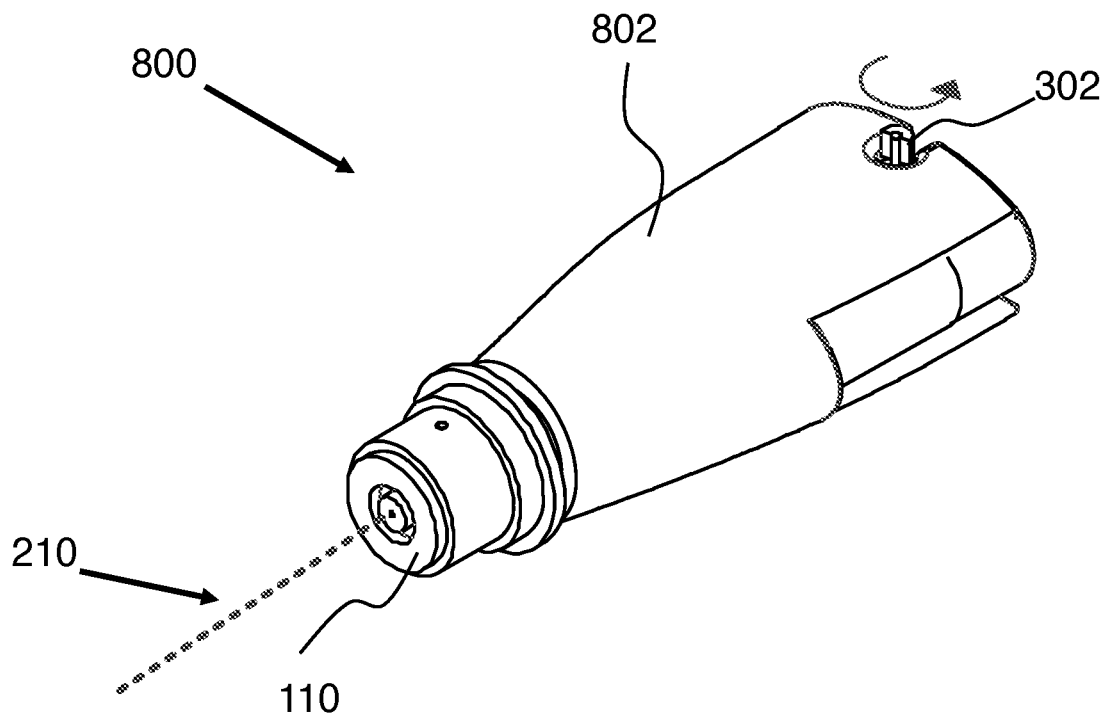
FIGS. 8A-B show a first embodiment of the invention having a disposable reservoir assembly.
Figure 8B:
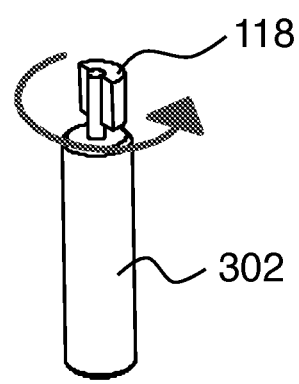
Figure 9A:
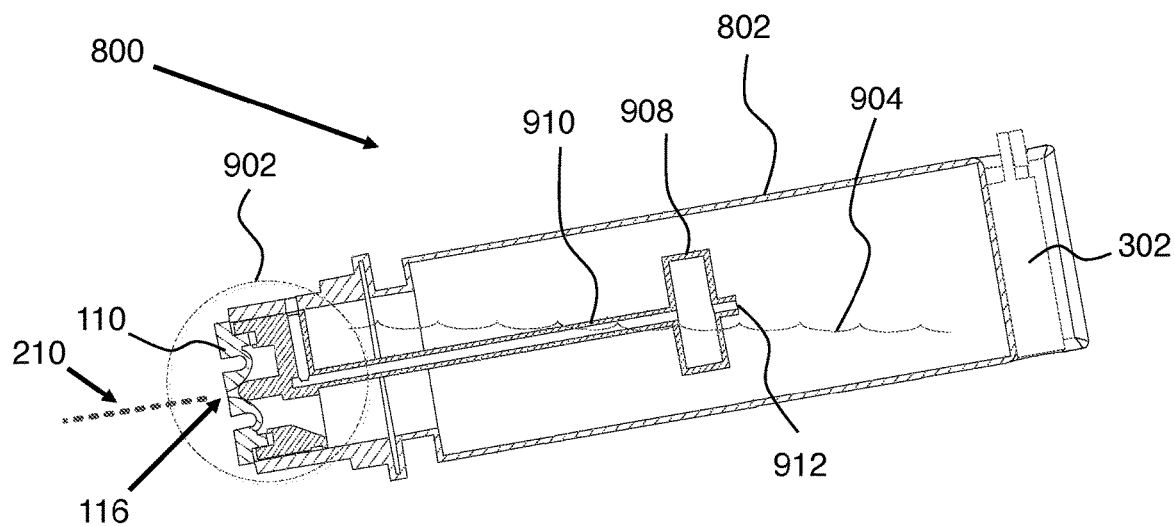
FIGS. 9A-C are detailed views of the example of FIGS. 8A-B.
Figure 9B:
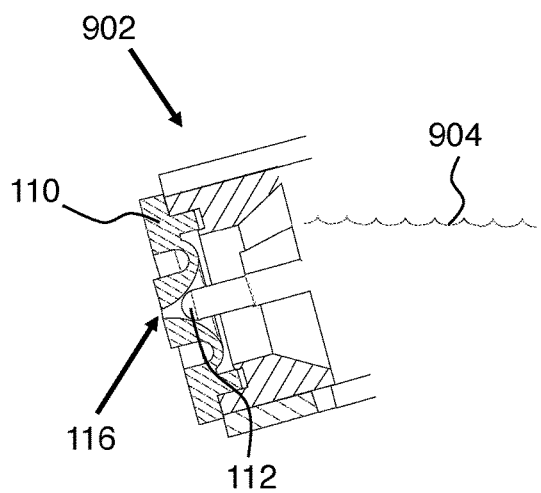
Figure 9C:
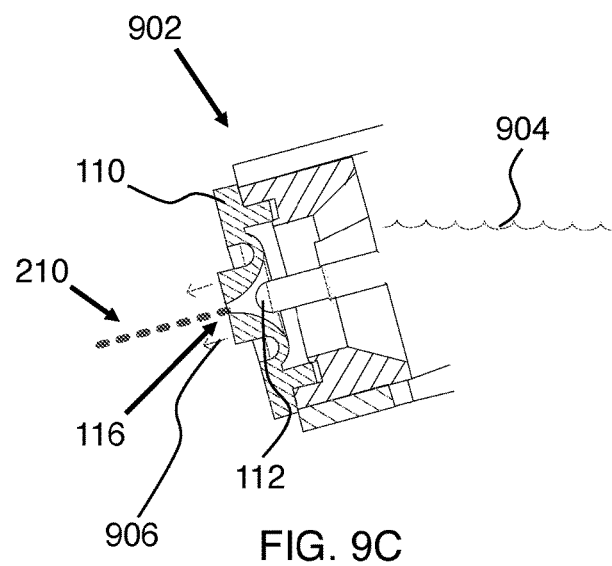

FIGS. 8A-8B illustrate a perspective view and FIGS. 9A-C illustrate a corresponding cross sectional view of a fluid delivery device 800. On FIG. 8A, the delivery device 800 includes a disposable bottle 802 and an aperture plate 110 installed at the neck of the bottle. A vibratory motor 302 is installed in the back end of the base unit which is in direct contact with the bottle 802. The aperture plate 110 provides frontal closure to bottle 802. FIG. 8B illustrates a perspective view of vibratory motor 302. As described above, this motor also includes eccentric mechanical load 118. In the following figures, the vibratory motor will consistently be referenced as 302 even in views where only eccentric mechanical load 118 is visible, for simplicity.

Referring to FIGS. 9A-C it can be seen that a check valve 902 includes an aperture plate 110 which has a conical or tapered aperture 116 that extends through its center thickness. Aperture 116 preferably has a large inlet opening in fluid communication with liquid 904 and a smaller exit opening though which fluid droplets 210 are dispensed. In this embodiment the aperture plate 110 is preferably made of flexible elastomer such as silicone rubber or TMA5APC elastomer made by KRAIBURG TPE CORP. Buford, GA Elastomers with Young modulus of elasticity in the range between 0.5 GPa to 2 GPa may also be used. The check valve 902 further includes a stationary hemispherical seal member 112 that seals the inlet opening of the conical aperture 116 providing a hermetically sealed closure. In the preferred embodiment the hemispherical member 112 is made of high density polyethylene (HDPE) which is harder than silicone thereby creating a tight closure as it engages in a pressure transmission relationship with the elastic aperture plate 110. The hemispherical member 112 engages in pressure transmission relationship with the conical aperture 116 with a preload force of between 0.1N-1N. The cracking pressure of check valve 902 is between 0.01-0.05 MPa.

As seen on FIG. 9A, the dispensing system includes a venting tube 910 that is configured to equalize the pressure inside and outside the bottle 802 as fluid is dispensed. The amount of fluid 904 that is contained in bottle 802 is less than half the total bottle volume. The venting tube 910 extends into the bottle such that the opening 912 of tube 910 is above the fluid level at any orientation that the device is held. The venting tube 910 can include a 0.22 micron filter 908 which separates airborne particles and microorganisms. The vibratory motor 302 is attached to the bottom of the bottle and generates cyclical stress that propagates to frontal end of the bottle and to the fluid therein.

FIGS. 9B and 9C illustrate check valve 902 in closed and open positions, respectively. FIG. 9B shows check valve 902 in a closed position. The tapered aperture 116 is engaged with the hemispherical member 112 to hermetically seal the aperture. FIG. 9C illustrates the check valve 902 in an open position. It can be seen that the central portion of the aperture plate 110 is displaced in the direction of arrows 906 due to the hydrodynamic pulses induced by the vibration. Consequently, check valve 902 opens and a stream of droplets 210 is ejected from the aperture.

Figure 10A:
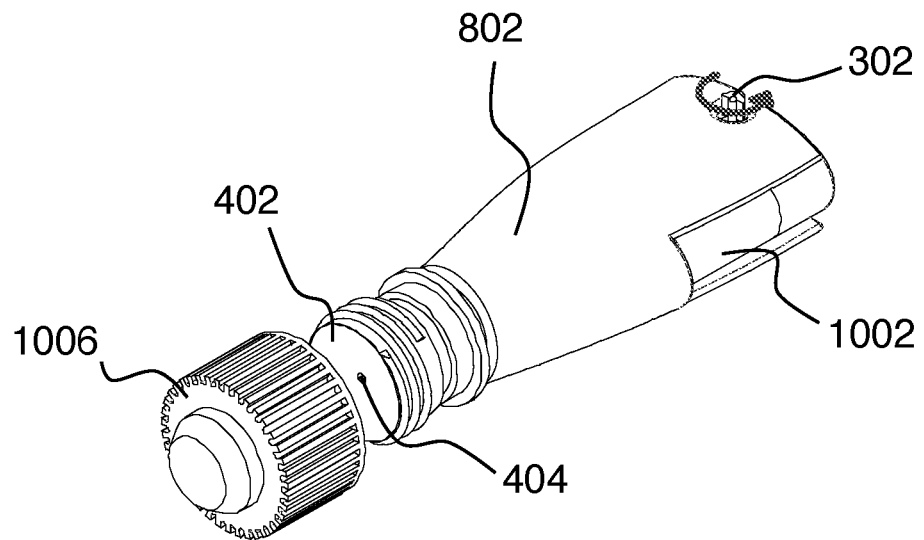
FIGS. 10A-C show a second embodiment of the invention having a disposable reservoir assembly.
Figure 10B:
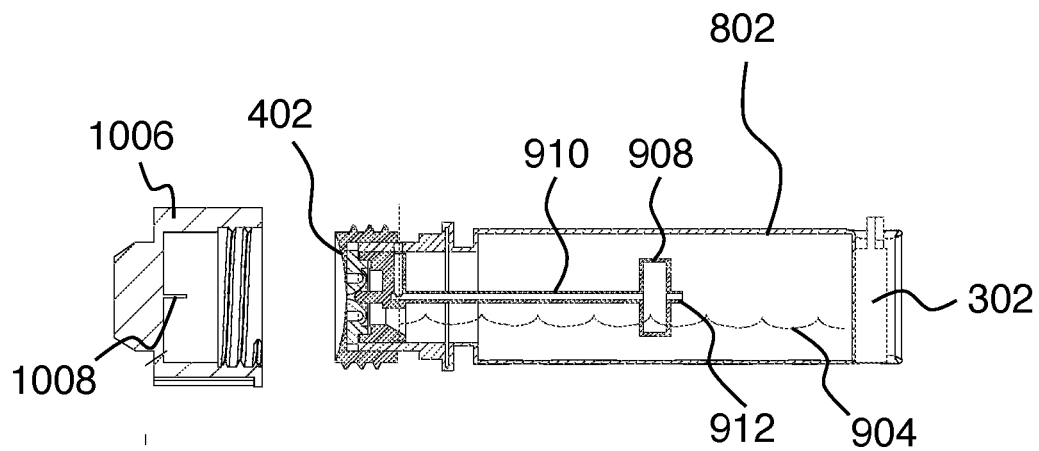
Figure 10C:
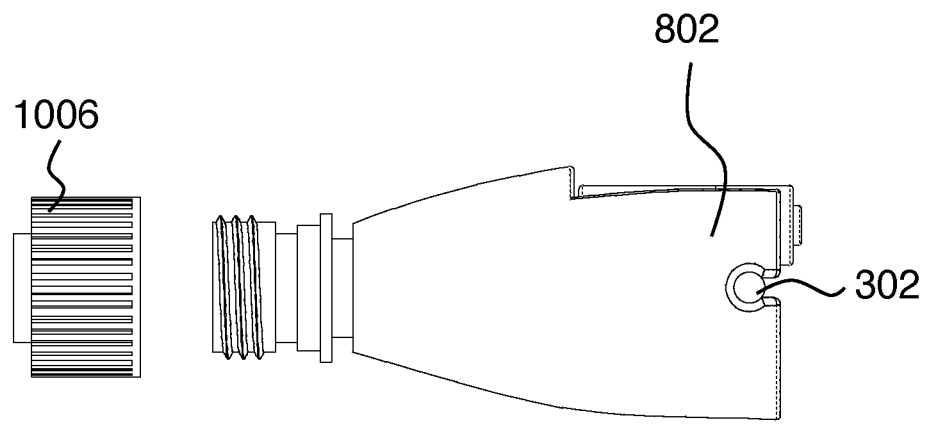

FIGS. 10A-C illustrate perspective and cross-sectional views of a dispensing system which include a closure cap 1006 and an alignment mirror 402. The closure cap 1006 is configured to seal the bottle during periods of non-use. The cap 1006 includes a central outwardly facing pin 1008 that enters the opening of the aperture to prevent residual liquid from drying out and clogging the outlet of the aperture when the cap is screwed on. The pin 1008 may include an antimicrobial coating to protect the outlet of the check valve from contamination. An alignment mirror 402 can be configured to assist the user in aligning the nozzle to the center of his eye. The mirror 402 has a concave reflective surface and includes a central opening 404 through which droplets are dispensed. The focal distance of mirror 402 can range from approximately 40 to 60 mm. Accordingly, when the central opening 404 is aligned with the optical axis of the eye and positioned at distance of 50 mm as an example, a clear magnified image of the user's eye is reflected on mirror which provides an indication that the device is aligned with the eye and positioned at the correct distance. Activation of the device when the image appears clear assures that the stream of droplets emitted from the opening 404 will deposit on the eye. The focal distance of the mirror may be between 40 to 60 mm.

FIG. 10B illustrates a cross sectional view of this dispensing system. The dispensing system of this example includes a venting tube as described above. The vibratory motor 302 is attached to the bottom of the bottle and generates cyclical stress that propagates to the frontal end of the bottle and to the fluid therein. FIG. 10C is a top view showing the mounting position of vibrational motor 302 in a C-slot at the rear end of bottle 802.

A DC motor 302 preferably generates centrifugal force of 0.1-1N and has a rotation speed of 10000-35000 RPM. The motor can be controlled by a timer circuit which sets the ON time required to deliver a dose of 8-12 micro-liter. The actuation on time is 60-200 ms depending on the rheology of the fluid in use. A timer circuit which incorporates 555 timer IC or a microprocessor-based timer may be used.

Figure 11:
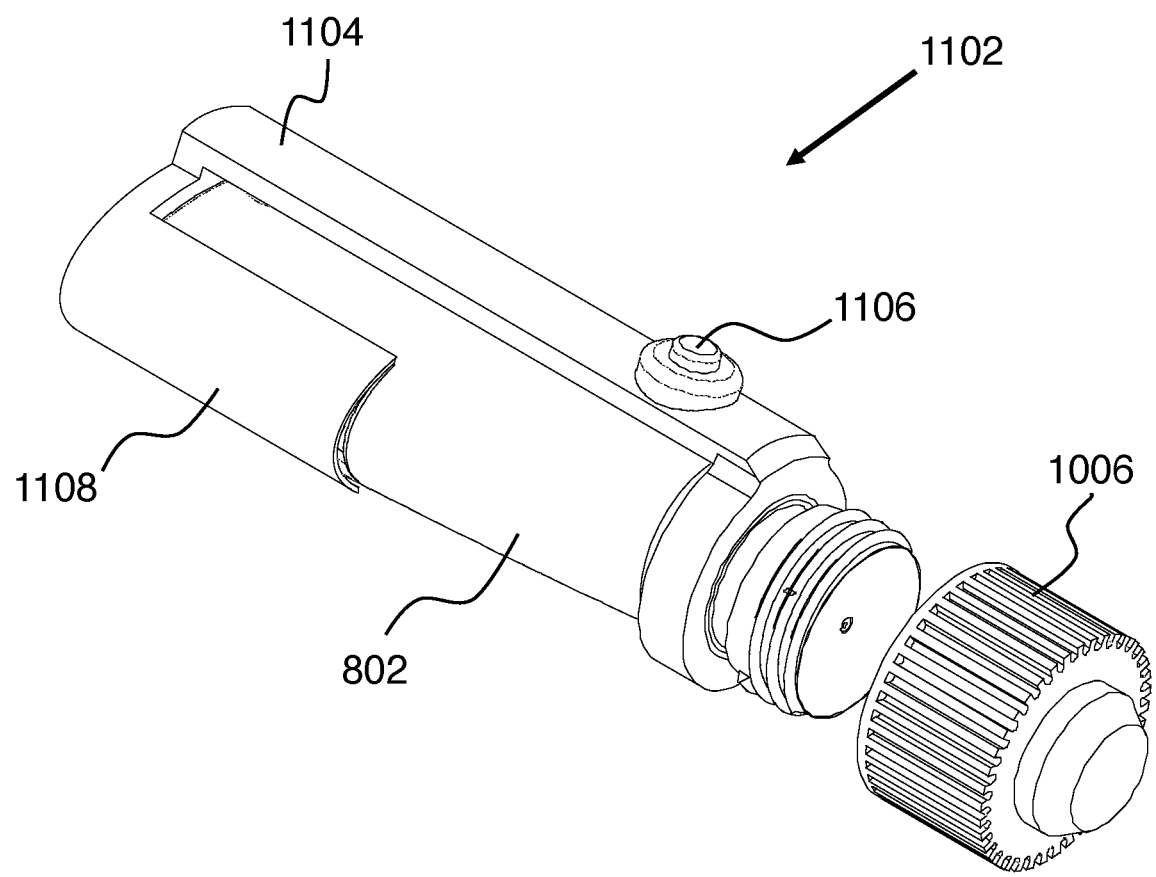
FIGS. 11-14 show a third embodiment of the invention having a disposable reservoir assembly.

FIG. 11 illustrates a dispensing system 1102 which includes a holding frame 1104 configured to retain the bottle 802, and further includes a battery compartment 1108, activation switch 1106 and an electronic circuit (not shown).

Figure 12:
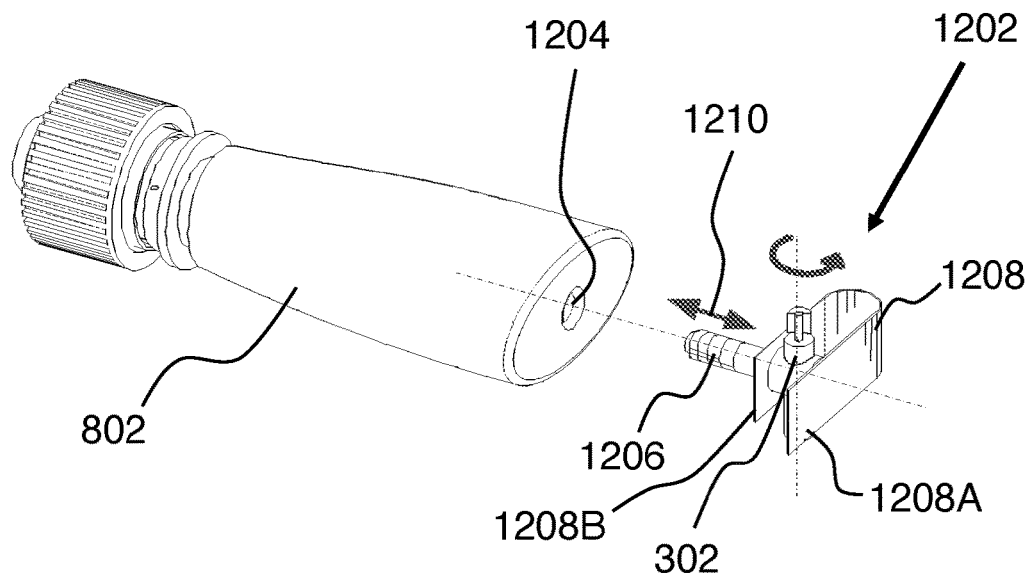
Figure 13:
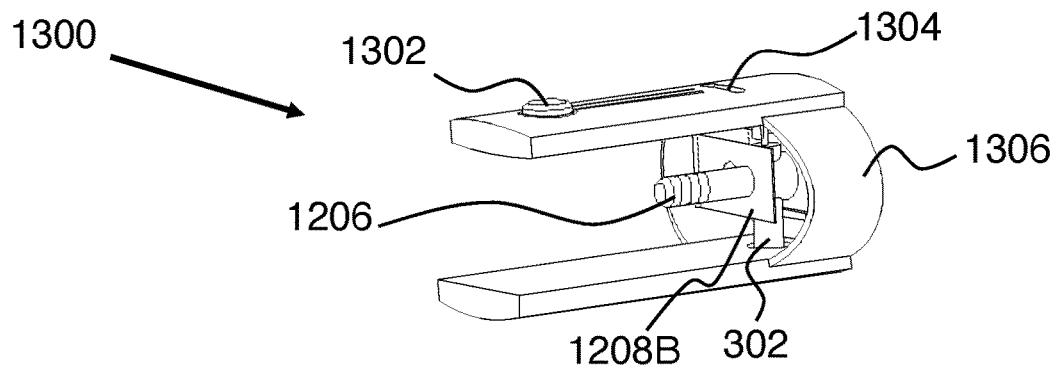
Figure 14:
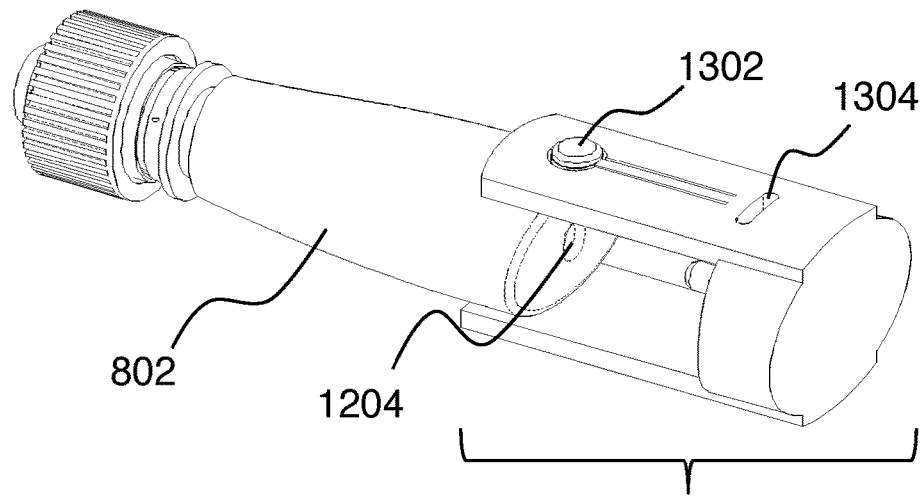

FIGS. 12-14 illustrate an alternative dispensing system which includes a disposable bottle 802 containing a fluid to be dispensed and reusable vibratory assembly 1300. Such a dispensing embodiment advantageously utilizes a disposable bottle 802 while desirably retaining the vibratory assembly 1300 for subsequent further uses, thereby providing an economical cost effective and environmentally friendly solution.

FIG. 12 shows the disposable bottle assembly 802 including a recessed hole 1204 at the base of bottle 802. The vibratory actuator 1202 includes a vibratory motor 302, a U-shaped spring member 1208 and a pin member 1206. The U-shape spring member 1208 has two legs wherein the first leg 1208A is constrained and a second leg 1208B is free to vibrate. The free leg 1208B is connected to vibratory motor 302 and to the pin member 1206. Rotation of the vibratory motor 302 causes the pin member 1206 to oscillate in the direction indicated by the arrow 1210. The oscillations are transmitted to the bottle 802 by engagement of the pin 1206 and hole 1204.

FIG. 13 is a perspective view of a reusable vibratory assembly 1300 which includes a housing 1306 configured to hold the vibratory actuator 1202 by providing a support structure to U-shaped spring arm 1208. A re-usable vibratory assembly 1300 can further includes a rechargeable lithium-ion battery (not shown), a mini-USB charging inlet 1304, a timer circuit and an actuation switch 1302.

The system can include a printed circuit board in a circuit (not shown) configured to control the operation of the vibratory motor. Specifically, upon activation the circuit turns the motor oscillation for a period of about 80 ms-150 ms to deliver a dose ranging from about 5 uls to about 50 uls depending on the aperture size, velocity of the motor and the time duration of the on cycle of the motor. This design enables the administration of fluids of relatively high viscosity not possible with other electromechanical approaches including smaller aperture systems associated with piezoelectric technology.

The electronic circuit may include a timer or a microprocessor-based timer. A microprocessor base circuit may also provide tracking and reporting of the patient eye drop usage, particularly for treatments involving a regimen of eyedrops administered at regular intervals over a long period of time. The electronic circuit may also include Bluetooth communication with a mobile device such as a phone or a tablet.

The electronic circuit may also include a means to identify the bottle in use and communicate the treatment regimen of eyedrop treatment to a mobile device.

The electronic system may further include a motion sensor or accelerometer that will measure the acceleration of the bottle and readjust the voltage setting to the vibrator motor. Such adjustment would be advantageous to obtain consistent dose while the fluid in the bottle is depleted and its mass and the dynamic of the system changes.

FIG. 14 illustrates prospective view of a dispensing system which includes disposable bottle 802 and reusable vibratory assembly 1300 in proximity when ready to engage.

Figure 15:
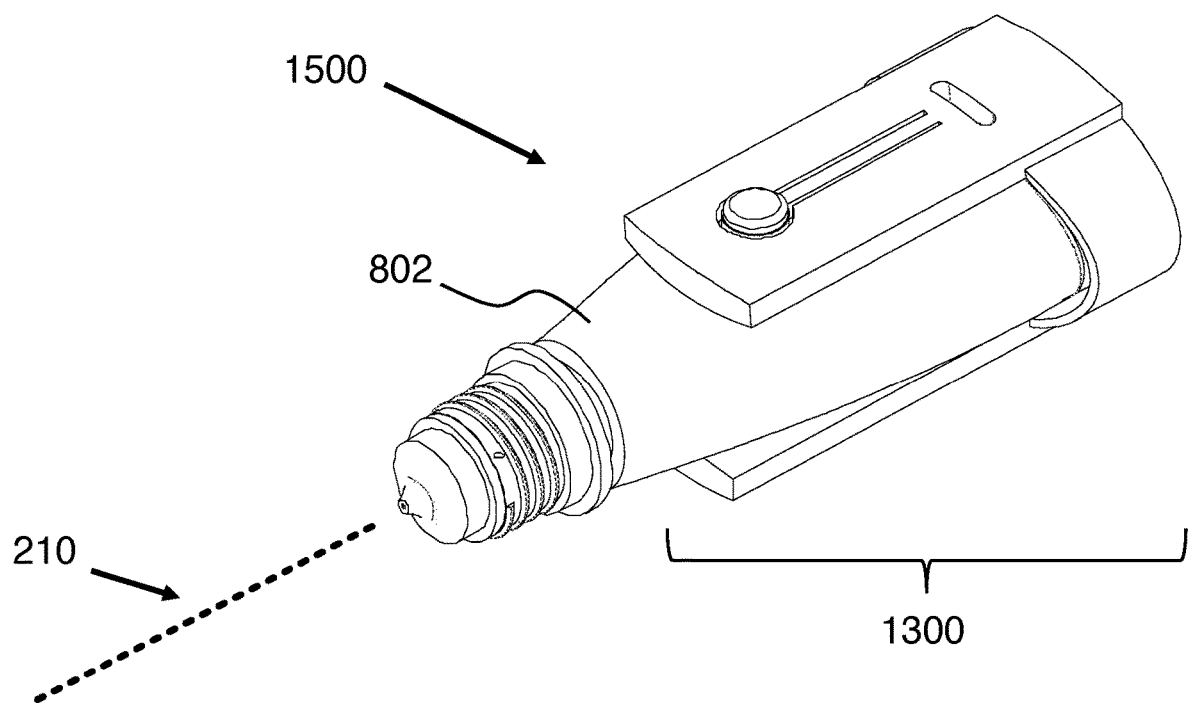
FIGS. 15-16 show a fourth embodiment of the invention having a disposable reservoir assembly.
Figure 16:
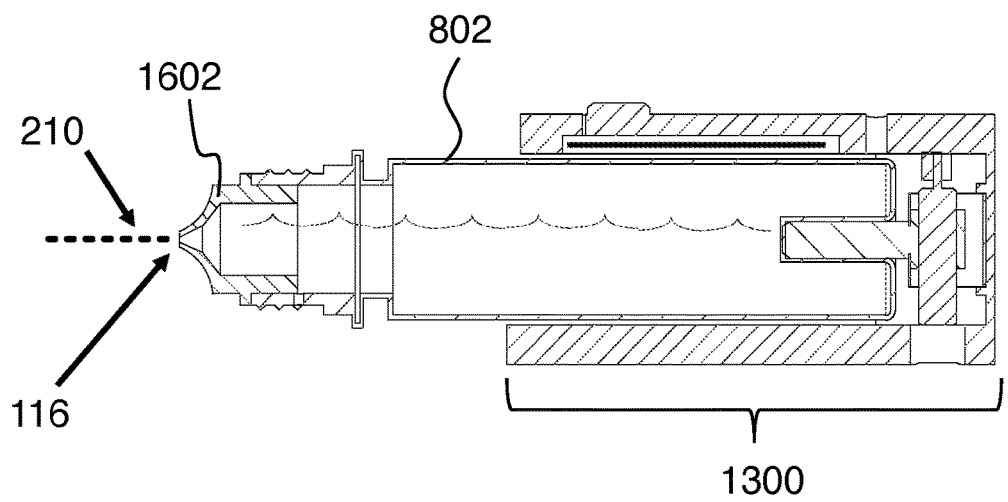

FIG. 15 is a perspective view of another dispensing system 1500 which includes a disposable bottle 802 and reusable vibratory assembly 1300 when fully assembled. FIG. 16 is a cross sectional view of the dispensing system of FIG. 15. Here the disposable bottle 802 utilizes a permanently open nozzle 1602 without a check valve; however, the bottle 802 may optionally include a check valve and air filter as previously described above. The nozzle 1602 includes a tapered aperture 116 with diameter ranging from 0.3 mm to 0.5 mm depending on the viscosity of the liquid in use. Preferably the bottle 802 and the nozzle 1602 are made of High-Density Polyethylene (HDPE) or Low-Density Polyethylene (LDPE).

Figure 17A:
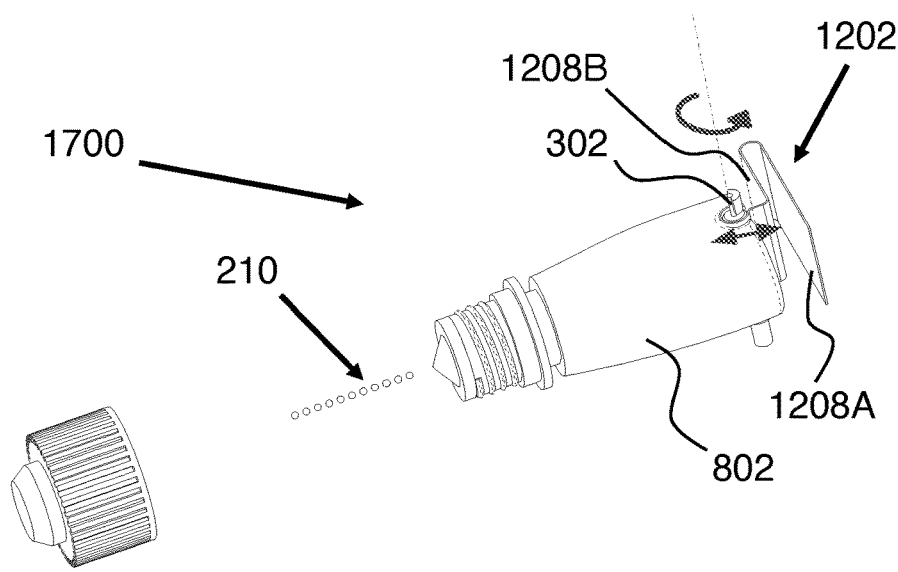
FIGS. 17A-C show a fifth embodiment of the invention having a disposable reservoir assembly.
Figures 17B, 17C:
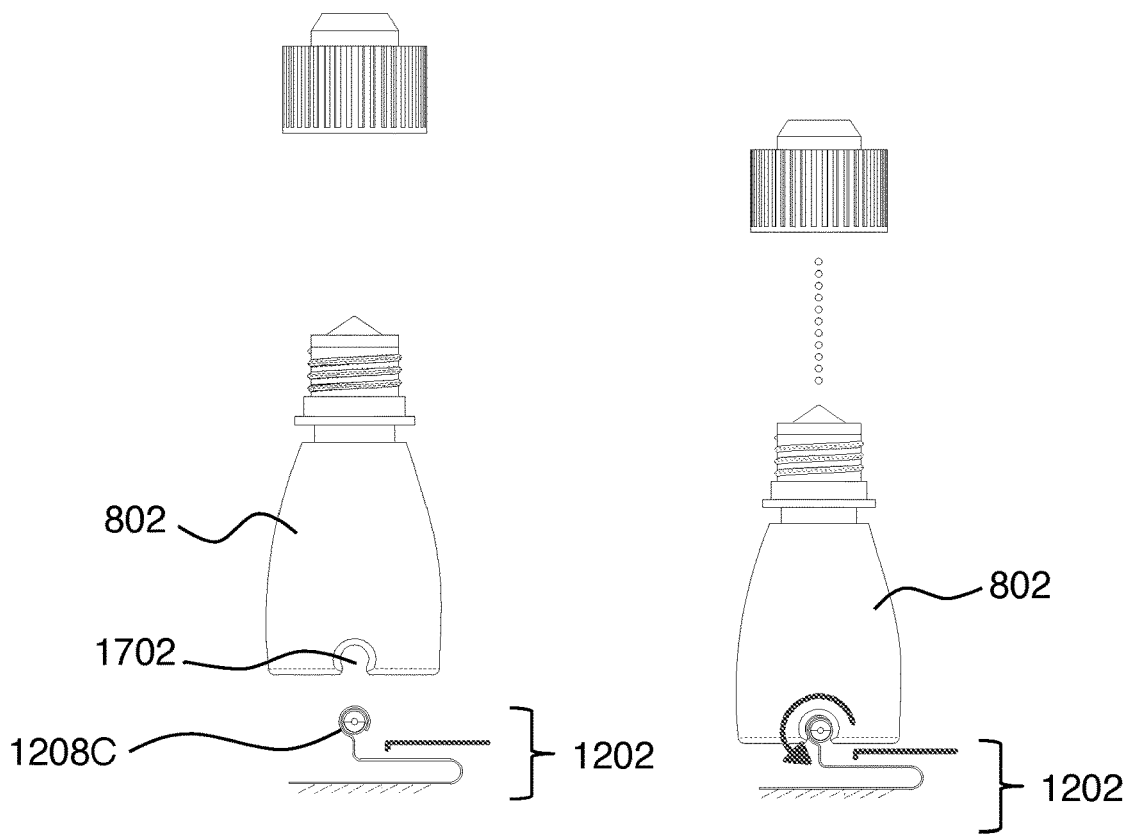

FIGS. 17A-C illustrate an alternative dispensing system 1700 which includes a disposable bottle 802 containing a fluid to be dispensed and reusable vibratory assembly 1202. Such a dispensing embodiment advantageously utilizes a disposable bottle 802 while desirably retaining the vibratory assembly 1202 for subsequent further uses, thereby providing an economical cost effective and environmentally friendly solution. Disposable bottle assembly 802 includes a C-shaped opening 1702 near the base of bottle 802.

The vibratory actuator 1202 includes a vibratory motor 302, and a U-shaped spring member 1208, as described above. The U-shape spring member has two legs where the first leg 1208A is constrained, and a second leg 1208B is free to vibrate. The free leg 1208B has a clip 1208C configured to clip vibratory motor 302.

The bottle 802 can be pushed toward the vibrator assembly such that the C-shape opening in the base of the bottle engages with the vibratory motor and further provides a tactile sensation to the user during this engagement. FIG. 17B illustrates the bottle disengaged from the vibratory assembly while FIG. 17C illustrates the bottle and the vibratory assembly fully engaged.

Figure 18A:
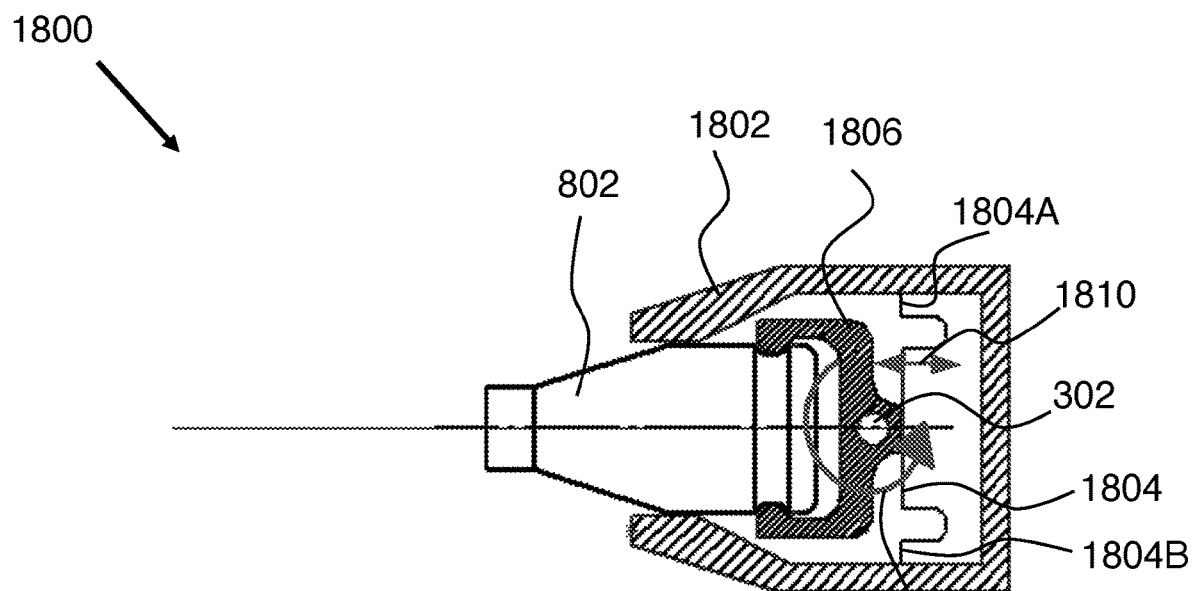
FIGS. 18A-B show a sixth embodiment of the invention having a disposable reservoir assembly.
Figure 18B:
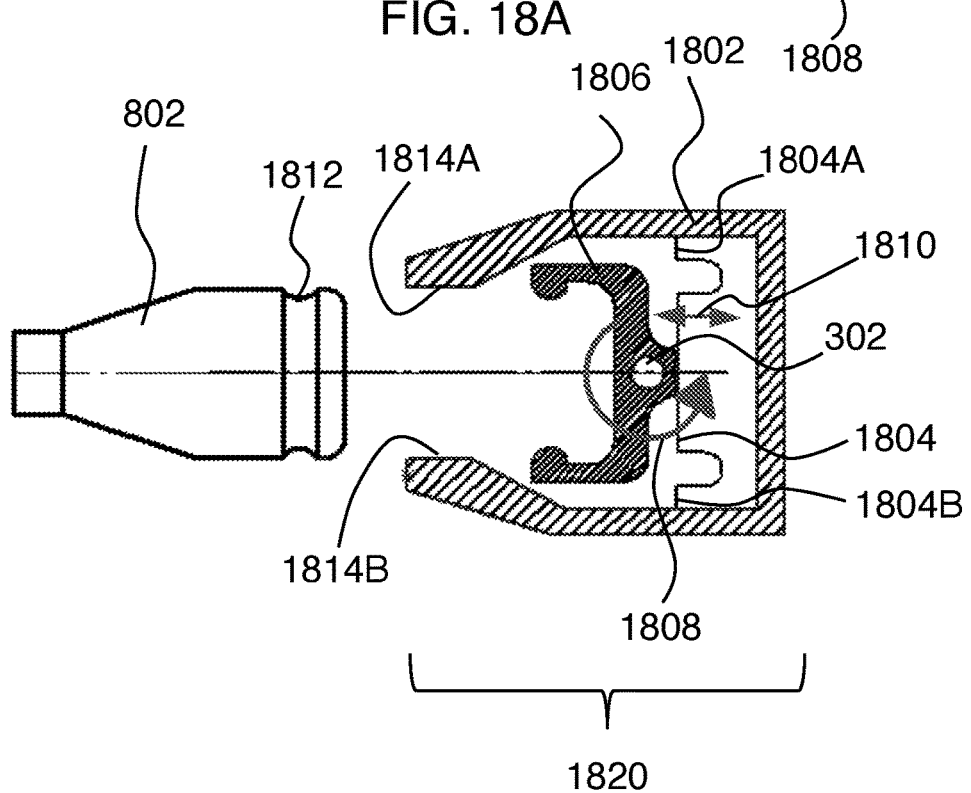

FIGS. 18A-B illustrate a dispensing system 1800 which includes a disposable bottle 802 containing a fluid to be dispensed and reusable vibratory assembly 1820. Such a dispensing embodiment advantageously utilizes a disposable bottle 802 while desirably retaining the vibratory assembly 1820 for subsequent further uses, thereby providing an economical cost effective and environmentally friendly solution.

Disposable bottle assembly 802 includes a groove 1812 at the base of bottle 802 configured to engage with vibratory C-Shape clamp member 1806.

Vibratory actuator 1820 includes a vibratory motor 302, a leaf spring 1804 and a C-Clamp 1806. Spring 1804 has two ends 1804A and 1804B which are fully supported by housing 1802 while C-Clamp member 1806 is connected at the center of the beam. Vibratory motor 302 is connected at the base of C-Clamp 1806. When vibratory motor 302 rotates as indicated by the arrow 1808 C-Clamp 1806 oscillates in the direction indicated by the arrow 1810. The vibratory oscillation is thereby transferred to bottle 802. Housing 1802 includes bearing surfaces 1814A and 1814B to provide support for bottle 802.

Notably, FIGS. 17A-18B demonstrate alternative ways relative to earlier embodiments that the vibratory member can engage with the base of the disposable bottle, which can be accomplished via a pin member, a clamp, groove(s), a spring member, or other compatible geometries that facilitate transfer of vibratory motion from the actuator to the bottle. For instance, instead of a C-clamp as described, a fully or partially circumferential groove (e.g. with a similar cross-section geometry as the aforementioned C-clamp) can be used to engage and secure the bottle in a removable fashion.

Figure 19A:
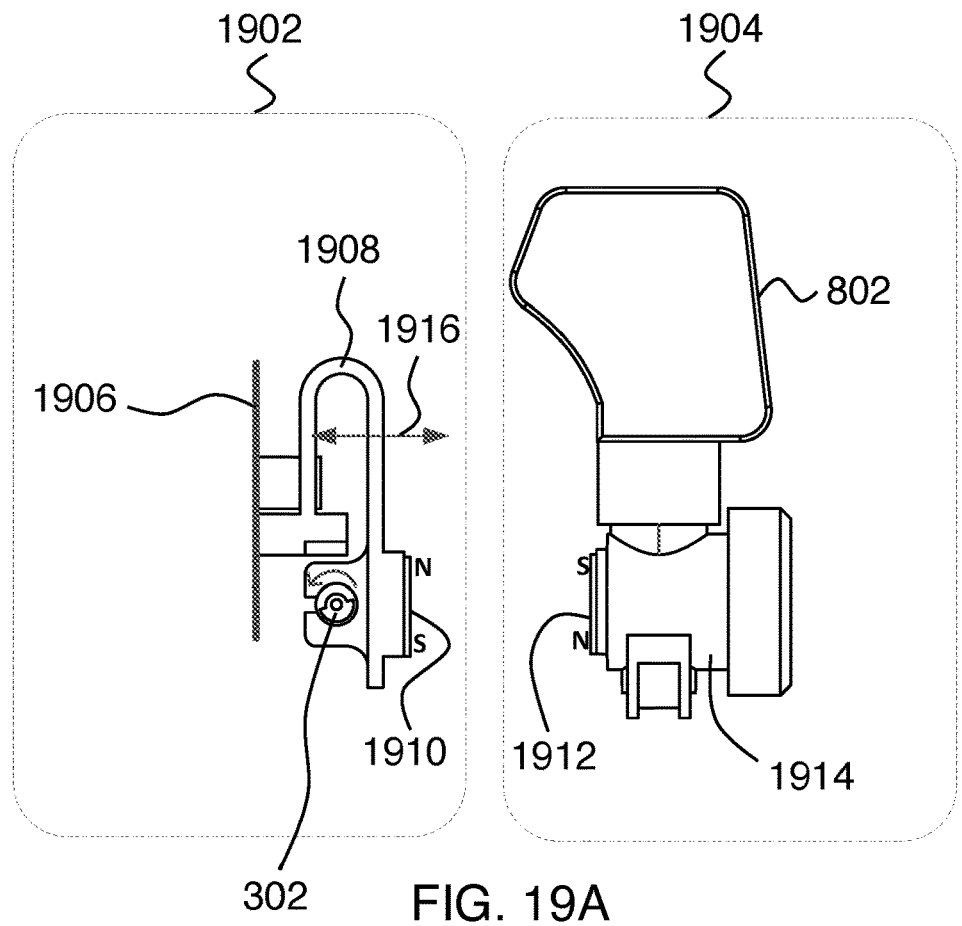
FIGS. 19A-B show a seventh embodiment of the invention having a disposable reservoir assembly.
Figure 19B:
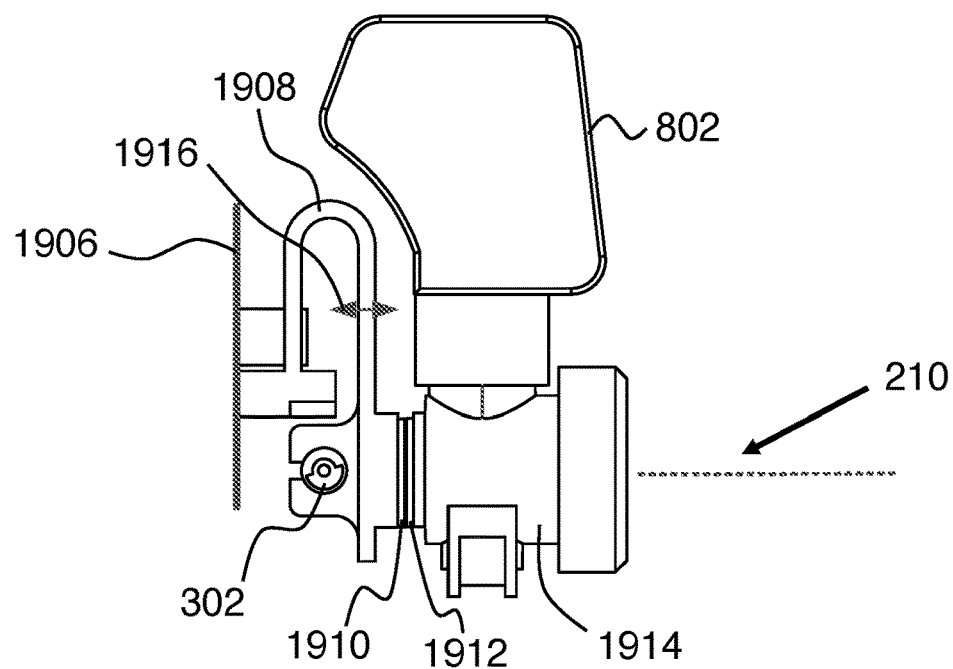

Another alternative for coupling a disposable bottle to a vibratory member is with magnets. In this way the bottle can be effectively coupled to the vibratory transducer but yet, it can also be effortlessly pulled out and replaced by the user. FIGS. 19A-B show an example of this.

FIG. 19A is a side view of the fluid delivery assembly showing the vibratory actuator assembly 1902 and the disposable ampoule assembly 1904 separately, each assembly is framed by a dotted line for clarity. It can be seen that each assembly had a permanent magnet 1910 and 1912 having opposite poles (N) and (S). The magnets 1910 and 1912 are preferably rare earth Neodymium alloy generally referred to as NdFeB magnets or NIB. The magnet plates can be coated with Nickel to prevent them from rusting. In an exemplary embodiment a magnet used was model B631 sold by K&J Magnetics Inc. FIG. 19B illustrates the ampoule assembly 1902 and a vibratory actuator 1904 fully engaged when the permanent magnets 1910 and 1912 are clamping the two assemblies together.

The vibratory transducer assembly 1902 includes a vibratory motor 302 that is attached to a flexible U-shape spring member 1908 configured to provide a degree of freedom for the vibratory displacement in the direction indicated by the arrow 1916. Here 1906 is a fixed attachment point for spring member 1908. Vibratory assembly 1902 include a permanent magnet 1910 having north (N) and south (S) poles. Disposable ampoule assembly 1904 includes an bottle 802, a valve assembly 1914 (operating as described above) with an aperture and permanent magnet 1912 having north (N) and south (S) poles. When the two magnets, 1910 and 1912 are engaged, the vibratory oscillation is transferred to the bottle assembly. Consequently, hydrodynamic cycles are developed within the valve assembly is eject fluid as described above.

The invention claimed is:

1. Apparatus for delivering a liquid to an eye of a patient, the apparatus comprising:
    a) a reservoir assembly; and
    b) an actuator assembly;
    c) wherein the reservoir assembly includes a reservoir configured to contain the liquid and a check valve, wherein the check valve includes an aperture through which the liquid can be dispensed and a pin member that engages with the aperture to provide a normally closed configuration of the check valve;

d) wherein the actuator assembly includes an actuator configured to provide a mechanical excitation to the reservoir assembly that generates a corresponding hydrodynamic excitation of the liquid;

e) wherein the hydrodynamic excitation of the liquid ejects the liquid through the aperture by elastically deforming the aperture to open the check valve; and f) wherein the actuator assembly can be connected to and disconnected from the reservoir assembly by a user, whereby the reservoir assembly is disposable.

2. The apparatus of claim 1, further comprising an optical sensor configured to provide a measurement of a frequency of the mechanical excitation.

3. The apparatus of claim 1, wherein a mechanical connection between the actuator assembly and the reservoir assembly is provided by a first permanent magnet disposed on the actuator assembly and a second permanent magnet disposed on the reservoir assembly.

4. The apparatus of claim 1, wherein a mechanical connection between the actuator assembly and the reservoir assembly is provided by a pin disposed on the actuator assembly configured to engage with a hole disposed on the reservoir assembly.

5. The apparatus of claim 1, wherein a mechanical connection between the actuator assembly and the reservoir assembly is provided by a ridge disposed on the actuator assembly configured to engage with a slot disposed on the reservoir assembly.

6. The apparatus of claim 1, wherein the actuator includes a vibration motor having an eccentric mechanical load relative to an axis of rotation of the vibration motor.

7. The apparatus of claim 6, wherein the reservoir assembly is supported by a flexible member, whereby operation of the vibration motor generates the hydrodynamic excitation of the liquid by oscillating the reservoir assembly.

8. The apparatus of claim 1, wherein the reservoir includes a vent.

9. The apparatus of claim 8, wherein the vent includes a filter configured to ensure that air that enters the reservoir is sterile.

10. The apparatus of claim 1, further comprising a concave mirror configured to provide an in-focus image of the patient's eye to the patient when the apparatus is positioned properly to deliver the liquid to the eye of the patient.

11. The apparatus of claim 1, wherein the actuator assembly further includes one or more components selected from the group consisting of: battery compartments, batteries, wireless communication devices, wired communication ports, and actuation switches.

* * * * *